(12) United States Patent
Davis et al.

(10) Patent No.: US 6,410,693 B1
(45) Date of Patent: Jun. 25, 2002

(54) INHIBITORS OF THE JNK SIGNAL TRANSDUCTION PATHWAY AND METHODS OF USE

(76) Inventors: Roger J. Davis, 53 Hickory Dr., Princeton, MA (US) 01541; Martin Dickens, Top Flat, 85 Coronation Road, Southville, Bristol B53 1AT (GB)

(*) Notice: Subject to any disclaimer, the term of this patent is extended or adjusted under 35 U.S.C. 154(b) by 0 days.

(21) Appl. No.: 09/419,587

(22) Filed: Oct. 18, 1999

Related U.S. Application Data

(62) Division of application No. 08/819,177, filed on Apr. 28, 1997, now Pat. No. 6,043,083.

(51) Int. Cl.$^7$ ............................................. C07K 16/00
(52) U.S. Cl. ................. 530/388.26; 530/350; 530/329; 530/325; 530/326; 530/327; 530/328; 514/2
(58) Field of Search ................. 530/350, 324–327, 530/389.2, 388.26; 514/2

(56) References Cited

U.S. PATENT DOCUMENTS 5,534,426 A * 7/1996 Karin et al. ................. 435/194

OTHER PUBLICATIONS

Ngo et al., Computational Complexity, Protein Structure Prediction and the Levinthal Paradox, 1994, Birkhauser Boston, vol. 14, pp. 491–495.*
Adams et al, GenBank Accession No. U62317, (submitted Jun. 26, 1996).
Andersson et al., GenBank Accession No. U79261, (submitted Nov. 22, 1996).
Choi et al., "Ste5 Tethers Multiple Protein Kinases in the MAP Kinase Cascade Required for Mating in Cerevisiae", Cell, 78:499–512, 1994.
Davis, "MAPKs: new JNK expands the group", TIBS 19:470–473, 1994.
Dérijard et al., "JNK1: A Protein Kinase Stimulated by UV Light and Ha–Ras That Binds and Phosphorylates the c–Jun Activation Domain", Cell, 76:1025–1037, 1994.
Dérijard et al., "Independent Human MAP Kinase Signal Transduction Pathways Defined by MEK and MKK Isoforms", Science, 267:682–685, 1995.
DiMari et al., "N–acetyl Cysteine Ameliorates Ischemic Renal Failure", Am. Physiological Soc., 272:F293–F298, 1997.
Faux et al., "Molecular Glue: Kinase Anchoring and Scaffold Proteins", Cell, 85:9–12, 1996.
Force et al., "Stress–Activated Protein Kinases in Cardiovascular Disease", American Heart Association, 78:947–953, 1996.

Galcheva–Gargova et al., "An Osmosensing Signal Transduction Pathway in Mammalian Cells", Science, 265:806–808, 1994.
Hibi et al., "Identification of an oncoprotein–and UV–responsive protein kinase that binds and potentiates the c–Jun activation domain", Genes & Dev., 7:2135–2148, 1993.
Lin et al., "Identification of a Dual Specificity Kinase That Activates the Jun Kinases and p38–Mpk2", Science, 268:286–290, 1995.
Mendelson et al., "Independent Regulation of JNK/p38 Mitogen–Activated Protein Kinases by Metabolic Oxidative Stress in the Liver", Proc. Nat'l. Acad. Sciences USA, 93:12908–12913, 1996.
McNeil et al., "Interaction of Autophosphorylated $Ca^{2+}$/Calmodul in–dependent Protein Kinase II with Neuronal Cytoskeletal Proteins", J. of Biol. Chemistry, 270:10043–10049, 1995.
Minden et al., "Differential Activation of ERK and JNK Mitogen–Activated Protein Kinases by Raf–1 and MEKK", Science, 266:1719–1723, 1994.
Pombo et al., "The Stress–Activated Protein Kinases Are Major c–Jun Amino–Terminal Kinases Activated by Ischemia and Reperfusion", J. of Biol. Chemistry, 269:26546–26551, 1994.
Riesgo–Escovar et al., Gene & Dev., 10:2745, 1996.
Sluss et al., "Signal Transduction by Tumor Necrosis Factor Mediated by JNK Protein Kinases", Mol. Cell. Biol., 14:8376–8384, 1994.
Sluss et al., Genes & Dev., 10:2745, 1996.
Whitmarsh et al., J. Mol. Med., 74:589, 1996.
Xia et al., "Opposing Effects of ERK and JNK–p38 MAP Kinases on Apoptosis", Science, 270:1326–1331, 1995.
Loregian et al., "Use of Vibrio spp. for expression of *escherichia coli* enterotoxin B subunit fusion proteins: . . . " Protein Expression and Purification 8:381–389, 1996.
Wang et al., "Intestinal absorption studies on peptide mimetic α–methyldopa prodrugs" J. of Pharmacy and Pharmacology 48(3):270–276, 1996.
Zhou et al., "Liposome–mediated cytoplamic delivery of proteins . . . " Immunomethods 4(3):229–235, 1994, Database Medline on STN Abstract.

* cited by examiner

*Primary Examiner*—Dave T. Nguyen
(74) *Attorney, Agent, or Firm*—Fish & Richardson P.C.

(57) ABSTRACT

JNK-interacting protein 1 (JIP-1), an inhibitor of the JNK1 protein, and methods of treating a pathological condition or of preventing the occurrence of a pathological condition in a patient by the administration of a therapeutically effective amount of JIP-1 polypeptides, peptides, peptide mimetics, or nucleic acids are described.

15 Claims, 6 Drawing Sheets

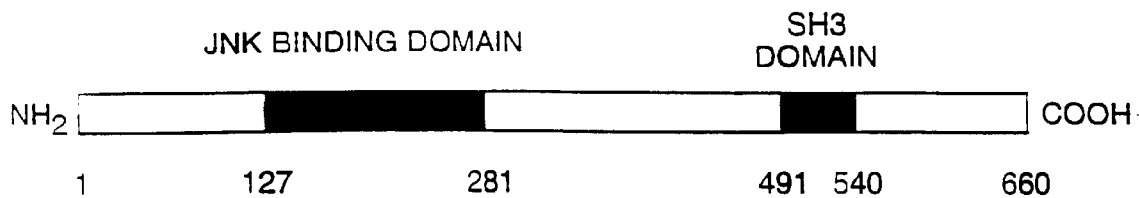

FIG. 1A

```
MAERESGLGGGAASPPAASPFLGLHIASPPNFRLTHDISLEEFEDEDLSE        50
ITDECGISLQCKDTLSLRPPRAGLLSAGSSGSAGSRLQAEMLQMDLIDAA       100
GDTPGAEDDEEEEDDELAAQRPGVGRPKAESNQDPAPRSQGQGPGTGSGD       150
TYRPKRPTTLNLPPQVPRSQDTLNNNSLGKKHSWQDRVSRSSSPLKTGEQ       200
TPPHEHICLSDELPPQGSPVPTQDRGTSTDSPCRRSAATQMAPPSGPPAT       250
APGGRGHSHRDRIHYQADVRLEATEEIYLTRVQRPPDPAEPTSTFMPPTE       300
SRMSVSSDPDPAAYSVTAGRPHPSISEEDEGFDCLSSPERAEPPGGGWRG       350
SLGEPPPPPRASLSSDTSALSYDSVKYTLVVDEHAQLELVSLRPCFGDYS       400
DESDSATVYDNCASASSPYESAIGEEYEEAPQPRPPTCLSEDSTPDEPDV       450
HFSKKFLNVFMSGRSRSSSAESFGLFSCVINGEEHEQTHRAIFRFVPRHE       500
DELELEVDDPLLVELQAEDYWYEAYNMRTGARGVFPAYYAIEVTKEPEHM       550
AALAKNSCVLEISVRGVKIGVKADDALEAKGNKCSHFFQLKNISFCGYHP       600
KNNKYFGFITKHPADHRFACHVFVSEDSTKALAESVGRAFQQFYKQFVEY       650
TCPTEDIYLE        660
```
(SEQ ID NO: 1)

FIG. 1B

```
CTCGAGGTCGACGGTATCGATAAGCTTGATATCGCTGTCCGGAGCCGCGCCCGCCCCAGCT
CAGTCCGAACCCGCGGCGGCGGCGGCCTCCTCCACGCGCCTCCGCTGCTGCCGCCGCCGC
CGCCGCCGCCGCCTCCCGCGCCGCTCTCCGCCCGGATGGCCAGGGCTGCACCCCGGAATGG
CGGAGCGAGAGAGCGGCCTGGGCGGGGGCGCCGCGTCCCCACCGGCCGCTTCCCCATTCCT
GGGACTGCACATCGCGTCGCCTCCCAATTTCAGGCTCACCCATGACATCAGCCTGGAGGAG
TTTGAGGATGAAGACCTTTCGGAGATCACTGACGAGTGTGGCATCAGCCTGCAGTGCAAAG
ACACCCTGTCTCTCCGGCCCCGCGCGCCGGGCTGCTGTCTGCGGGTAGCAGCGGCAGCGC
GGGGAGCCGGCTGCAGGCGGAGATGCTGCAGATGGACCTGATCGACGCGGCAGGTGACACT
CCGGGCGCCGAGGACGACGAGGAGGAGGAGGACGACGAGCTCGCTGCCCAACGACCAGGAG
TGGGGCCTCCCAAAGCGGAGTCCAACCAGGATCCGGCGCCTCGCAGCCAGGGCCAGGGCCC
GGGCACAGGCAGCGGAGACACCTACCGACCCAAGAGGCCTACCACGCTCAACCTTTTCCCG
CAGGTGCCGCGGTCTCAGGACACGCTGAATAATAACTCTTTAGGCAAAAAGCACAGTTGGC
AGGACCGTGTGTCTCGATCATCCTCCCCTCTGAAGACAGGAGAACAGACGCCTCCACATGA
ACACATCTGCCTGAGTGATGAGCTGCCACCCCAGGGCAGTCCTGTTCCCACCCAGGACCGC
GGCACTTCCACCGACAGCCCTTGTCGCCGAAGTGCAGCCACCCAGATGGCACCTCCAAGCG
GTCCCCCTGCCACTGCTCCTGGTGGCCGGGGCCACTCCCATCGAGACCGAATCCACTACCA
GGCAGATGTGCGGCTCGAGGCGACTGAGGAGATCTACCTGACCCCAGTGCAGAGGCCCCCA
GACCCTGCAGAACCCACCTCCACCTTCATGCCACCCACGGAGAGCCGGATGTCAGTTAGCT
CGGATCCAGACCCTGCCGCTTACTCTGTAACTGCGGGGCGGCCACACCCCTCCATCAGTGA
AGAGGATGAGGGCTTCGACTGCCTGTCATCCCCAGAGCGAGCTGAGCCACCAGGTGGAGGG
TGGCGGGGAAGCCTCGGGGAGCCACCACCGCCTCCACGGGCCTCACTGAGCTCGGACACCA
GCGCACTGTCCTACGACTCGGTCAAGTACACACTGGTGGTGGATGAACATGCCCAGCTTGA
GTTGGTGAGCCTGCGGCCGTGCTTTGGAGATTACAGTGACGAAAGCGACTCTGCCACTGTC
TATGACAACTGTGCCTCTGCCTCCTCGCCCTACGAGTCAGCCATTGGTGAGGAGTATGAGG
AGGCCCCTCAGCCCCGGCCTCCCACCTGCCTCTCAGAGGACTCCACCCCGGATGAGCCTGA
TGTCCACTTCTCTAAGAAGTTTCTGAATGTCTTCATGAGTGGCCGCTCTCGTTCCTCCAGT
GCTGAGTCCTTTGGGCTGTTCTCCTGCGTCATCAATGGGGAGGAGCATGAGCAAACCCATC
GGGCTATATTCAGGTTTGTGCCTCGGCATGAAGATGAACTTGAGCTGGAAGTGGATGACCC
CCTGCTGGTGGAGCTGCAGGCAGAAGACTATTGGTATGAGGCCTATAACATGCGCACCGGA
GCCCGCGGGTCTTCCCTGCCTACTATGCCATTGAGGTCACCAAGGAGCCTGAGCACATGG
CAGCCCTTGCCAAAAACAGCTGTGTCCTTGAGATCAGTGTCAGGGGTGTCAAGATAGGCGT
CAAAGCTGATGATGCTCTGGAGGCCAAGGGAAATAAATGTAGCCACTTCTTCCAGCTAAAG
AACATCTCTTTCTGTGGATACCATCCAAAGAATAACAAGTACTTTGGGTTTATCACTAAGC
ACCCTGCTGACCACCGGTTTGCCTGCCATGTCTTTGTGTCTGAAGATTCCACCAAAGCCCT
GGCGGAGTCTGTGGGCGTGCATTTCAGCAGTTCTACAAGCAGTTTGTGGAGTATACCTGT
CCTACAGAAGATATCTACTTGGAGTAGCAGCACCCCCACTCTCTGCAGCCCCTCAGCCCCA
AGCCAGTGCAAGGACAGCTGGCTGCTGACAGGATGTGGTACTGCCACAAAAGAATGGGGGA
ATGAGGGCTGTTGGGTCGGGGGGCCGGGGTTTGGGGAGAGGCAGATGCAGTTTATTGTAA
TATATGGGGTTAGATTAATCTATGGAGGACAGTACAGGCTCTCTGGGGACTGGGGAAGGGT
GGGGCTGGGGGTGGGGGTCAGGCCCCTGGCCACAGAGGGACTCCCTAGGAACAGAGGCA
CTGTCCCATCCTGGGCCTGTTTCATGCTAGGGCCCTGGCTTTCTGGCTCTTGGCTCCTGC
CTTGACAAAGCCCATGCCACCTGGAAGTGTCCAGCTTCCCTTGTCCCCACCTTGACCGGAG
CCCTGAGCTCAGGCTGAGCCCACGCACCTCCAAAGGACTTTCCAGTAAGGAAATGGCAACG
TGTGACCGTGGAGACCCTGTTCTCATCTGTGGGCCTCTGGGCAGCTCCAACCTCCAGCCT
GGCTAGCACACAGGTCCTCGCAAGGTTGTGTGTGCAAGGAGAGGGCCACAGTAAGCCCCAT
CTGCCAGGAAAGGAGGCCTCTTAGCTGGCCCCAGCCAGCCGGTCACTGTCTTGTCACCTG
GCTACTATTAAAGTGCCATCTCGTGC
```

(SEQ ID NO: 2)

FIG. 1C

| | | |
|---|---|---|
| JIP-1 | SGDTYRPKRPTTLNLFPQVPRSQDTLN | (SEQ ID NO: 3) |
| c-Jun | YSNPK I L . QSM . . . . ADPVGSLKPHLR | (SEQ ID NO: 5) |
| ATF-2 | HLAVHKH . HEM . . KFG ARND . V I VAD | (SEQ ID NO: 6) |
| Concensus | K    TL | |

FIG. 2

| | | |
|---|---|---|
| JIP-1 | SGDTYRPKRPTT L N LFPQVPRSQDTLN | (SEQ ID NO: 3) |
| (159-162)G | ................GGGG................ | (SEQ ID NO: 7) |
| T159g | ................G................ | (SEQ ID NO: 8) |
| L160g | ................G................ | (SEQ ID NO: 9) |
| L162G | ................G................ | (SEQ ID NO:10) |
| K155G | ................G................ | (SEQ ID NO:11) |
| Control | NSLGTDDTQYSRRPPKVRQPNPTFTLL | (SEQ ID NO:12) |

FIG. 3

SEQUENCE LISTING

```
(1) GENERAL INFORMATION:

(iii) NUMBER OF SEQUENCES: 30

(2) INFORMATION FOR SEQ ID NO:1:

(i) SEQUENCE CHARACTERISTICS:
         (A) LENGTH: 660 amino acids
         (B) TYPE: amino acid
         (D) TOPOLOGY: linear (ii) MOLECULE TYPE: protein (v) FRAGMENT TYPE: internal (ix) FEATURE:
         (D) OTHER INFORMATION: JIP-1 protein (xi) SEQUENCE DESCRIPTION: SEQ ID NO:1:

Met Ala Glu Arg Glu Ser Gly Leu Gly Gly Ala Ala Ser Pro Pro
 1               5                  10                  15

Ala Ala Ser Pro Phe Leu Gly Leu His Ile Ala Ser Pro Pro Asn Phe
                20                  25                  30

Arg Leu Thr His Asp Ile Ser Leu Glu Glu Phe Glu Asp Glu Asp Leu
            35                  40                  45

Ser Glu Ile Thr Asp Glu Cys Gly Ile Ser Leu Gln Cys Lys Asp Thr
    50                  55                  60

Leu Ser Leu Arg Pro Pro Arg Ala Gly Leu Leu Ser Ala Gly Ser Ser
65                  70                  75                  80

Gly Ser Ala Gly Ser Arg Leu Gln Ala Glu Met Leu Gln Met Asp Leu
                85                  90                  95

Ile Asp Ala Ala Gly Asp Thr Pro Gly Ala Glu Asp Asp Glu Glu Glu
            100                 105                 110

Glu Asp Asp Glu Leu Ala Ala Gln Arg Pro Gly Val Gly Pro Pro Lys
        115                 120                 125

Ala Glu Ser Asn Gln Asp Pro Ala Pro Arg Ser Gln Gly Gln Gly Pro
    130                 135                 140

Gly Thr Gly Ser Gly Asp Thr Tyr Arg Pro Lys Arg Pro Thr Thr Leu
145                 150                 155                 160

Asn Leu Phe Pro Gln Val Pro Arg Ser Gln Asp Thr Leu Asn Asn Asn
```

-continued

```
               165                 170                 175
Ser Leu Gly Lys Lys His Ser Trp Gln Asp Arg Val Ser Arg Ser Ser
            180                 185                 190
Ser Pro Leu Lys Thr Gly Glu Gln Thr Pro Pro His Glu His Ile Cys
            195                 200                 205
Leu Ser Asp Glu Leu Pro Pro Gln Gly Ser Pro Val Pro Thr Gln Asp
            210                 215                 220
Arg Gly Thr Ser Thr Asp Ser Pro Cys Arg Ser Ala Ala Thr Gln
225                 230                 235                 240
Met Ala Pro Pro Ser Gly Pro Pro Ala Thr Ala Pro Gly Gly Arg Gly
                245                 250                 255
His Ser His Arg Asp Arg Ile His Tyr Gln Ala Asp Val Arg Leu Glu
            260                 265                 270
Ala Thr Glu Glu Ile Tyr Leu Thr Pro Val Gln Arg Pro Pro Asp Pro
            275                 280                 285
Ala Glu Pro Thr Ser Thr Phe Met Pro Pro Thr Glu Ser Arg Met Ser
            290                 295                 300
Val Ser Ser Asp Pro Asp Pro Ala Ala Tyr Ser Val Thr Ala Gly Arg
305                 310                 315                 320
Pro His Pro Ser Ile Ser Glu Glu Asp Glu Gly Phe Asp Cys Leu Ser
                325                 330                 335
Ser Pro Glu Arg Ala Glu Pro Pro Gly Gly Gly Trp Arg Gly Ser Leu
            340                 345                 350
Gly Glu Pro Pro Pro Pro Arg Ala Ser Leu Ser Ser Asp Thr Ser
            355                 360                 365
Ala Leu Ser Tyr Asp Ser Val Lys Tyr Thr Leu Val Val Asp Glu His
            370                 375                 380
Ala Gln Leu Glu Leu Val Ser Leu Arg Pro Cys Phe Gly Asp Tyr Ser
385                 390                 395                 400
Asp Glu Ser Asp Ser Ala Thr Val Tyr Asp Asn Cys Ala Ser Ala Ser
                405                 410                 415
Ser Pro Tyr Glu Ser Ala Ile Gly Glu Glu Tyr Glu Glu Ala Pro Gln
            420                 425                 430
Pro Arg Pro Pro Thr Cys Leu Ser Glu Asp Ser Thr Pro Asp Glu Pro
            435                 440                 445
Asp Val His Phe Ser Lys Lys Phe Leu Asn Val Phe Met Ser Gly Arg
            450                 455                 460
Ser Arg Ser Ser Ser Ala Glu Ser Phe Gly Leu Phe Ser Cys Val Ile
465                 470                 475                 480
Asn Gly Glu Glu His Glu Gln Thr His Arg Ala Ile Phe Arg Phe Val
                485                 490                 495
Pro Arg His Glu Asp Glu Leu Glu Leu Glu Val Asp Asp Pro Leu Leu
            500                 505                 510
Val Glu Leu Gln Ala Glu Asp Tyr Trp Tyr Glu Ala Tyr Asn Met Arg
            515                 520                 525
Thr Gly Ala Arg Gly Val Phe Pro Ala Tyr Tyr Ala Ile Glu Val Thr
            530                 535                 540
Lys Glu Pro Glu His Met Ala Ala Leu Ala Lys Asn Ser Cys Val Leu
545                 550                 555                 560
Glu Ile Ser Val Arg Gly Val Lys Ile Gly Val Lys Ala Asp Asp Ala
                565                 570                 575
Leu Glu Ala Lys Gly Asn Lys Cys Ser His Phe Phe Gln Leu Lys Asn
            580                 585                 590
```

```
Ile Ser Phe Cys Gly Tyr His Pro Lys Asn Asn Lys Tyr Phe Gly Phe
        595                 600                 605

Ile Thr Lys His Pro Ala Asp His Arg Phe Ala Cys His Val Phe Val
        610                 615                 620

Ser Glu Asp Ser Thr Lys Ala Leu Ala Glu Ser Val Gly Arg Ala Phe
625                 630                 635                 640

Gln Gln Phe Tyr Lys Gln Phe Val Glu Tyr Thr Cys Pro Thr Glu Asp
                645                 650                 655

Ile Tyr Leu Glu
            660

(2) INFORMATION FOR SEQ ID NO:2:

(i) SEQUENCE CHARACTERISTICS:
        (A) LENGTH: 2832 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding S equence
        (B) LOCATION: 180...2159
        (D) OTHER INFORMATION: JIP-1 cDNA (xi) SEQUENCE DESCRIPTION: SEQ ID NO:2:

CTCGAGGTCG ACGGTATCGA TAAGCTTGAT ATCGCTGTCC GGAGCCGCGC CCGCCCCAGC     60

TCAGTCCGAA CCCCGCGGCG GCGGCGGCCT CCTCCACGCG CCTCCGCTGC TGCCGCCGCC    120

GCCGCCGCCG CCGCCTCCCG CGCCGCTCTC CGCCCGGATG GCCAGGGCTG CACCCCGGA    179

ATG GCG GAG CGA GAG AGC GGC CTG GGC GGG GGC GCC GCG TCC CCA CCG    227
Met Ala Glu Arg Glu Ser Gly Leu Gly Gly Gly Ala Ala Ser Pro Pro
1               5                   10                  15

GCC GCT TCC CCA TTC CTG GGA CTG CAC ATC GCG TCG CCT CCC AAT TTC    275
Ala Ala Ser Pro Phe Leu Gly Leu His Ile Ala Ser Pro Pro Asn Phe
                20                  25                  30

AGG CTC ACC CAT GAC ATC AGC CTG GAG GAG TTT GAG GAT GAA GAC CTT    323
Arg Leu Thr His Asp Ile Ser Leu Glu Glu Phe Glu Asp Glu Asp Leu
            35                  40                  45

TCG GAG ATC ACT GAC GAG TGT GGC ATC AGC CTG CAG TGC AAA GAC ACC    371
Ser Glu Ile Thr Asp Glu Cys Gly Ile Ser Leu Gln Cys Lys Asp Thr
        50                  55                  60

CTG TCT CTC CGG CCC CCG CGC GCC GGG CTG CTG TCT GCG GGT AGC AGC    419
Leu Ser Leu Arg Pro Pro Arg Ala Gly Leu Leu Ser Ala Gly Ser Ser
65                  70                  75                  80

GGC AGC GCG GGG AGC CGG CTG CAG GCG GAG ATG CTG CAG ATG GAC CTG    467
Gly Ser Ala Gly Ser Arg Leu Gln Ala Glu Met Leu Gln Met Asp Leu
                85                  90                  95

GTC GAC GCG GCA GGT GAC ACT CCG GGC GCC GAG GAC GAC GAG GAG GAG    515
Ile Asp Ala Ala Gly Asp Thr Pro Gly Ala Glu Asp Asp Glu Glu Glu
            100                 105                 110

GAG GAC GAC GAG CTC GCT GCC CAA CGA CCA GGA GTG GGG CCT CCC AAA    563
Glu Asp Asp Glu Leu Ala Ala Gln Arg Pro Gly Val Gly Pro Pro Lys
        115                 120                 125

GCG GAG TCC AAC CAG GAT CCG GCG CCT CGC AGC CAG GGC CAG GGC CCG    611
Ala Glu Ser Asn Gln Asp Pro Ala Pro Arg Ser Gln Gly Gln Gly Pro
130                 135                 140

GGC ACA GGC AGC GGA GAC ACC TAC CGA CCC AAG AGG CCT ACC ACG CTC    659
Gly Thr Gly Ser Gly Asp Thr Tyr Arg Pro Lys Arg Pro Thr Thr Leu
145                 150                 155                 160
```

```
AAC CTT TTC CCG CAG GTG CCG CGG TCT CAG GAC ACG CTG AAT AAT AAC     707
Asn Leu Phe Pro Gln Val Pro Arg Ser Gln Asp Thr Leu Asn Asn Asn
            165                 170                 175

TCT TTA GGC AAA AAG CAC AGT TGG CAG GAC CGT GTG TCT CGA TCA TCC     755
Ser Leu Gly Lys Lys His Ser Trp Gln Asp Arg Val Ser Arg Ser Ser
            180                 185                 190

TCC CCT CTG AAG ACA GGA GAA CAG ACG CCT CCA CAT GAA CAC ATC TGC     803
Ser Pro Leu Lys Thr Gly Glu Gln Thr Pro Pro His Glu His Ile Cys
            195                 200                 205

CTG AGT GAT GAG CTG CCA CCC CAG GGC AGT CCT GTT CCC ACC CAG GAC     851
Leu Ser Asp Glu Leu Pro Pro Gln Gly Ser Pro Val Pro Thr Gln Asp
210             215                 220

CGC GGC ACT TCC ACC GAC AGC CCT TGT CGC CGA AGT GCA GCC ACC CAG     899
Arg Gly Thr Ser Thr Asp Ser Pro Cys Arg Arg Ser Ala Ala Thr Gln
225             230                 235                 240

ATG GCA CCT CCA AGC GGT CCC CCT GCC ACT GCT CCT GGT GGC CGG GGC     947
Met Ala Pro Pro Ser Gly Pro Pro Ala Thr Ala Pro Gly Gly Arg Gly
                245                 250                 255

CAC TCC CAT CGA GAC CGA ATC CAC TAC CAG GCA GAT GTG CGG CTC GAG     995
His Ser His Arg Asp Arg Ile His Tyr Gln Ala Asp Val Arg Leu Glu
                260                 265                 270

GCG ACT GAG GAG ATC TAC CTG ACC CCA GTG CAG AGG CCC CCA GAC CCT    1043
Ala Thr Glu Glu Ile Tyr Leu Thr Pro Val Gln Arg Pro Pro Asp Pro
            275                 280                 285

GCA GAA CCC ACC TCC ACC TTC ATG CCA CCC ACG GAG AGC CGG ATG TCA    1091
Ala Glu Pro Thr Ser Thr Phe Met Pro Pro Thr Glu Ser Arg Met Ser
        290                 295                 300

GTT AGC TCG GAT CCA GAC CCT GCC GCT TAC TCT GTA ACT GCG GGG CGG    1139
Val Ser Ser Asp Pro Asp Pro Ala Ala Tyr Ser Val Thr Ala Gly Arg
305             310                 315                 320

CCA CAC CCC TCC ATC AGT GAA GAG GAT GAG GGC TTC GAC TGC CTG TCA    1187
Pro His Pro Ser Ile Ser Glu Glu Asp Glu Gly Phe Asp Cys Leu Ser
                325                 330                 335

TCC CCA GAG CGA GCT GAG CCA CCA GGT GGA GGG TGG CGG GGA AGC CTC    1235
Ser Pro Glu Arg Ala Glu Pro Pro Gly Gly Gly Trp Arg Gly Ser Leu
                340                 345                 350

GGG GAG CCA CCA CCG CCT CCA CGG GCC TCA CTG AGC TCG GAC ACC AGC    1283
Gly Glu Pro Pro Pro Pro Pro Arg Ala Ser Leu Ser Ser Asp Thr Ser
            355                 360                 365

GCA CTG TCC TAC GAC TCG GTC AAG TAC ACA CTG GTG GTG GAT GAA CAT    1331
Ala Leu Ser Tyr Asp Ser Val Lys Tyr Thr Leu Val Val Asp Glu His
370             375                 380

GCC CAG CTT GAG TTG GTG AGC CTG CGG CCG TGC TTT GGA GAT TAC AGT    1379
Ala Gln Leu Glu Leu Val Ser Leu Arg Pro Cys Phe Gly Asp Tyr Ser
385             390                 395                 400

GAC GAA AGC GAC TCT GCC ACT GTC TAT GAC AAC TGT GCC TCT GCC TCC    1427
Asp Glu Ser Asp Ser Ala Thr Val Tyr Asp Asn Cys Ala Ser Ala Ser
                405                 410                 415

TCG CCC TAC GAG TCA GCC ATT GGT GAG GAG TAT GAG GAG GCC CCT CAG    1475
Ser Pro Tyr Glu Ser Ala Ile Gly Glu Glu Tyr Glu Glu Ala Pro Gln
                420                 425                 430

CCC CGG CCT CCC ACC TGC CTC TCA GAG GAC TCC ACC CCG GAT GAG CCT    1523
Pro Arg Pro Pro Thr Cys Leu Ser Glu Asp Ser Thr Pro Asp Glu Pro
            435                 440                 445

GAT GTC CAC TTC TCT AAG AAG TTT CTG AAT GTC TTC ATG AGT GGC CGC    1571
Asp Val His Phe Ser Lys Lys Phe Leu Asn Val Phe Met Ser Gly Arg
        450                 455                 460

TCT CGT TCC TCC AGT GCT GAG TCC TTT GGG CTG TTC TCC TGC GTC ATC    1619
Ser Arg Ser Ser Ser Ala Glu Ser Phe Gly Leu Phe Ser Cys Val Ile
```

```
                465                 470                 475                 480
AAT GGG GAG GAG CAT GAG CAA ACC CAT CGG GCT ATA TTC AGG TTT GTG              1667
Asn Gly Glu Glu His Glu Gln Thr His Arg Ala Ile Phe Arg Phe Val
                        485                 490                 495

CCT CGG CAT GAA GAT GAA CTT GAG CTG GAA GTG GAT GAC CCC CTG CTG              1715
Pro Arg His Glu Asp Glu Leu Glu Leu Glu Val Asp Asp Pro Leu Leu
                500                 505                 510

GTG GAG CTG CAG GCA GAA GAC TAT TGG TAT GAG GCC TAT AAC ATG CGC              1763
Val Glu Leu Gln Ala Glu Asp Tyr Trp Tyr Glu Ala Tyr Asn Met Arg
            515                 520                 525

ACC GGA GCC CGC GGG GTC TTC CCT GCC TAC TAT GCC ATT GAG GTC ACC              1811
Thr Gly Ala Arg Gly Val Phe Pro Ala Tyr Tyr Ala Ile Glu Val Thr
        530                 535                 540

AAG GAG CCT GAG CAC ATG GCA GCC CTT GCC AAA AAC AGC TGT GTC CTT              1859
Lys Glu Pro Glu His Met Ala Ala Leu Ala Lys Asn Ser Cys Val Leu
545                 550                 555                 560

GAG ATC AGT GTC AGG GGT GTC AAG ATA GGC GTC AAA GCT GAT GAT GCT              1907
Glu Ile Ser Val Arg Gly Val Lys Ile Gly Val Lys Ala Asp Asp Ala
                565                 570                 575

CTG GAG GCC AAG GGA AAT AAA TGT AGC CAC TTC TTC CAG CTA AAG AAC              1955
Leu Glu Ala Lys Gly Asn Lys Cys Ser His Phe Phe Gln Leu Lys Asn
                580                 585                 590

ATC TCT TTC TGT GGA TAC CAT CCA AAG AAT AAC AAG TAC TTT GGG TTT              2003
Ile Ser Phe Cys Gly Tyr His Pro Lys Asn Asn Lys Tyr Phe Gly Phe
            595                 600                 605

ATC ACT AAG CAC CCT GCT GAC CAC CGG TTT GCC TGC CAT GTC TTT GTG              2051
Ile Thr Lys His Pro Ala Asp His Arg Phe Ala Cys His Val Phe Val
        610                 615                 620

TCT GAA GAT TCC ACC AAA GCC CTG GCG GAG TCT GTG GGG CGT GCA TTT              2099
Ser Glu Asp Ser Thr Lys Ala Leu Ala Glu Ser Val Gly Arg Ala Phe
625                 630                 635                 640

CAG CAG TTC TAC AAG CAG TTT GTG GAG TAT ACC TGT CCT ACA GAA GAT              2147
Gln Gln Phe Tyr Lys Gln Phe Val Glu Tyr Thr Cys Pro Thr Glu Asp
                645                 650                 655

ATC TAC TTG GAG TAGCAGCACC CCCACTCTCT GCAGCCCCTC AGCCCCAAGC                  2199
Ile Tyr Leu Glu
            660

CAGTGCAAGG ACAGCTGGCT GCTGACAGGA TGTGGTACTG CCACAAAAGA ATGGGGAAT             2259

GAGGGCTGTT GGGTCGGGGG GGCCGGGGTT TGGGGAGAGG CAGATGCAGT TTATTGTAAT            2319

ATATGGGGTT AGATTAATCT ATGGAGGACA GTACAGGCTC TCTGGGGACT GGGGAAGGGT            2379

GGGGCTGGGG GGTGGGGGGT CAGGCCCCTG CCACAGAGG GACTCCCTAG GAACAGAGGC             2439

ACTGTCCCAT CCTGGGCCTG TTTCATGCTA GGGGCCCTGG CTTTCTGGCT CTTGGCTCCT            2499

GCCTTGACAA AGCCCATGCC ACCTGGAAGT GTCCAGCTTC CCTTGTCCCC ACCTTGACCG            2559

GAGCCCTGAG CTCAGGCTGA GCCCACGCAC CTCCAAAGGA CTTTCCAGTA AGGAAATGGC            2619

AACGTGTGAC CGTGGAGACC CTGTTCTCAT CTGTGGGGCC TCTGGGCAGC TCCAACCTCC            2679

AGCCTGGCTA GCACACAGGT CCTCGCAAGG TTGTGTGTGC AAGGAGAGGG CCACAGTAAG            2739

CCCCATCTGC CAGGAAAAGG AGGCCTCTTA GCTGGCCCCA GCCAGCCGGT CACTGTCTTG            2799

TCACCTGGCT ACTATTAAAG TGCCATCTCG TGC                                        2832
```

(2) INFORMATION FOR SEQ ID NO:3:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
 (D) OTHER INFORMATION: JIP-1 protein, amino acids 148-174

(xi) SEQUENCE DESCRIPTION: SEQ ID NO:3:

Ser Gly Asp Thr Tyr Arg Pro Lys Arg Pro Thr Thr Leu Asn Leu Phe
1               5                   10                  15

Pro Gln Val Pro Arg Ser Gln Asp Thr Leu Asn
            20                  25

(2) INFORMATION FOR SEQ ID NO:4:

(i) SEQUENCE CHARACTERISTICS:
  (A) LENGTH: 155 amino acids
  (B) TYPE: amino acid
  (D) TOPOLOGY: linear (ii) MOLECULE TYPE: protein (ix) FEATURE:
  (D) OTHER INFORMATION: JIP-1 protein, amino acids 127-281

(xi) SEQUENCE DESCRIPTION: SEQ ID NO:4:

Pro Lys Ala Glu Ser Asn Gln Asp Pro Ala Pro Arg Ser Gln Gly Gln
1               5                   10                  15

Gly Pro Gly Thr Gly Ser Gly Asp Thr Tyr Arg Pro Lys Arg Pro Thr
            20                  25                  30

Thr Leu Asn Leu Phe Pro Gln Val Pro Arg Ser Gln Asp Thr Leu Asn
        35                  40                  45

Asn Ser Leu Gly Lys Lys His Ser Trp Gln Asp Arg Val Ser Arg
    50                  55                  60

Ser Ser Ser Pro Leu Lys Thr Gly Glu Gln Thr Pro Pro His Glu His
65                  70                  75                  80

Ile Cys Leu Ser Asp Glu Leu Pro Pro Gln Gly Ser Pro Val Pro Thr
                85                  90                  95

Gln Asp Arg Gly Thr Ser Thr Asp Ser Pro Cys Arg Arg Ser Ala Ala
            100                 105                 110

Thr Gln Met Ala Pro Pro Ser Gly Pro Pro Ala Thr Ala Pro Gly Gly
        115                 120                 125

Arg Gly His Ser His Arg Asp Arg Ile His Tyr Gln Ala Asp Val Arg
    130                 135                 140

Leu Glu Ala Thr Glu Glu Ile Tyr Leu Thr Pro
145                 150                 155

(2) INFORMATION FOR SEQ ID NO:5:

(i) SEQUENCE CHARACTERISTICS:
  (A) LENGTH: 27 amino acids
  (B) TYPE: amino acid
  (D) TOPOLOGY: linear (ii) MOLECULE TYPE: peptide (ix) FEATURE:
  (D) OTHER INFORMATION: c-Jun JNK-binding domain (xi) SEQUENCE DESCRIPTION: SEQ ID NO:5:

Tyr Ser Asn Pro Lys Ile Leu Lys Gln Ser Met Thr Leu Asn Leu Ala
1               5                   10                  15

Asp Pro Val Gly Ser Leu Lys Pro His Leu Arg
            20                  25

(2) INFORMATION FOR SEQ ID NO:6:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: ATF-2 JNK-binding domain (xi) SEQUENCE DESCRIPTION: SEQ ID NO:6:

```
His Leu Ala Val His Lys His Lys His Glu Met Thr Leu Lys Phe Gly
 1               5                  10                  15

Pro Ala Arg Asn Asp Ser Val Ile Val Ala Asp
            20                  25
```

(2) INFORMATION FOR SEQ ID NO:7:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: JIP-1 mutant (159-162) G (xi) SEQUENCE DESCRIPTION: SEQ ID NO:7:

```
Ser Gly Asp Thr Tyr Arg Pro Lys Arg Pro Thr Gly Gly Gly Gly Phe
 1               5                  10                  15

Pro Gln Val Pro Arg Ser Gln Asp Thr Leu Asn
            20                  25
```

(2) INFORMATION FOR SEQ ID NO:8:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: JIP-1 mutant T159G (xi) SEQUENCE DESCRIPTION: SEQ ID NO:8:

```
Ser Gly Asp Thr Tyr Arg Pro Lys Arg Pro Thr Gly Leu Asn Leu Phe
 1               5                  10                  15

Pro Gln Val Pro Arg Ser Gln Asp Thr Leu Asn
            20                  25
```

(2) INFORMATION FOR SEQ ID NO:9:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: JIP-1 mutant L160G (xi) SEQUENCE DESCRIPTION: SEQ ID NO:9:

```
Ser Gly Asp Thr Tyr Arg Pro Lys Arg Pro Thr Thr Gly Asn Leu Phe
  1               5                  10                  15

Pro Gln Val Pro Arg Ser Gln Asp Thr Leu Asn
             20                  25
```

(2) INFORMATION FOR SEQ ID NO:10:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: JIP-1 mutant L162G (xi) SEQUENCE DESCRIPTION: SEQ ID NO:10:

```
Ser Gly Asp Thr Tyr Arg Pro Lys Arg Pro Thr Thr Leu Asn Gly Phe
  1               5                  10                  15

Pro Gln Val Pro Arg Ser Gln Asp Thr Leu Asn
             20                  25
```

(2) INFORMATION FOR SEQ ID NO:11:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: JIP-1 mutant K155G (xi) SEQUENCE DESCRIPTION: SEQ ID NO:11:

```
Ser Gly Asp Thr Tyr Arg Pro Gly Arg Pro Thr Thr Leu Asn Leu Phe
  1               5                  10                  15

Pro Gln Val Pro Arg Ser Gln Asp Thr Leu Asn
             20                  25
```

(2) INFORMATION FOR SEQ ID NO:12:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: control peptide (xi) SEQUENCE DESCRIPTION: SEQ ID NO:12:

```
Asn Ser Leu Gly Thr Asp Asp Thr Gln Tyr Ser Arg Arg Pro Pro Lys
  1               5                  10                  15

Val Arg Gln Pro Asn Pro Thr Phe Thr Leu Leu
             20                  25
```

(2) INFORMATION FOR SEQ ID NO:13:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (ix) FEATURE:
    (D) OTHER INFORMATION: JIP-1 amino acids 491-540 (SH3 domain)

(xi) SEQUENCE DESCRIPTION: SEQ ID NO:13:

Ala Ile Phe Arg Glu Val Pro Arg His Glu Asp Glu Leu Glu Leu Glu
 1               5                  10                  15

Val Asp Asp Pro Leu Leu Val Glu Leu Gln Ala Glu Asp Tyr Trp Tyr
                20                  25                  30

Glu Ala Tyr Asn Met Arg Thr Gly Ala Arg Gly Val Phe Pro Ala Tyr
            35                  40                  45

Tyr Ala
    50

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (D) OTHER INFORMATION: Flag eptiope (xi) SEQUENCE DESCRIPTION: SEQ ID NO:14:

Asp Tyr Lys Asp Asp Asp Asp Lys
 1               5

(2) INFORMATION FOR SEQ ID NO:15:

(i) SEQUENCE CHARACTERISTICS:
        (A) LENGTH: 76 amino acids
        (B) TYPE: amino acid
        (D) TOPOLOGY: linear (ii) MOLECULE TYPE: peptide (ix) FEATURE:
        (D) OTHER INFORMATION: JIP-1 amino acids 127-202

(xi) SEQUENCE DESCRIPTION: SEQ ID NO:15:

Pro Lys Ala Glu Ser Asn Gln Asp Pro Ala Pro Arg Ser Gln Gly Gln
 1               5                  10                  15

Gly Pro Gly Thr Gly Ser Gly Asp Thr Tyr Arg Pro Lys Arg Pro Thr
                20                  25                  30

Thr Leu Asn Leu Phe Pro Gln Val Pro Arg Ser Gln Asp Thr Leu Asn
            35                  40                  45

Asn Asn Ser Leu Gly Lys Lys His Ser Trp Gln Asp Arg Val Ser Arg
        50                  55                  60

Ser Ser Ser Pro Leu Lys Thr Gly Glu Gln Thr Pro
65                  70                  75

(2) INFORMATION FOR SEQ ID NO:16:

(i) SEQUENCE CHARACTERISTICS:
        (A) LENGTH: 79 amino acids
        (B) TYPE: amino acid
        (D) TOPOLOGY: linear (ii) MOLECULE TYPE: peptide (ix) FEATURE:
        (D) OTHER INFORMATION: JIP-1 amino acids 203-281

(xi) SEQUENCE DESCRIPTION: SEQ ID NO:16:

```
Pro His Glu His Ile Cys Leu Ser Asp Glu Leu Pro Pro Gln Gly Ser
 1               5                  10                  15

Pro Val Pro Thr Gln Asp Arg Gly Thr Ser Thr Asp Ser Pro Cys Arg
             20                  25                  30

Arg Ser Ala Ala Thr Gln Met Ala Pro Pro Ser Gly Pro Pro Ala Thr
         35                  40                  45

Ala Pro Gly Gly Arg Gly His Ser His Arg Asp Arg Ile His Tyr Gln
     50                  55                  60

Ala Asp Val Arg Leu Glu Ala Thr Glu Glu Ile Tyr Leu Thr Pro
 65                  70                  75
```

(2) INFORMATION FOR SEQ ID NO:17:

(i) SEQUENCE CHARACTERISTICS:
        (A) LENGTH: 77 amino acids
        (B) TYPE: amino acid
        (D) TOPOLOGY: linear (ii) MOLECULE TYPE: peptide (ix) FEATURE:
        (D) OTHER INFORMATION: JIP-1 amino acids 164-240

(xi) SEQUENCE DESCRIPTION: SEQ ID NO:17:

```
Pro Gln Val Pro Arg Ser Gln Asp Thr Leu Asn Asn Ser Leu Gly
 1               5                  10                  15

Lys Lys His Ser Trp Gln Asp Arg Val Ser Arg Ser Ser Pro Leu
             20                  25                  30

Lys Thr Gly Glu Gln Thr Pro Pro His Glu His Ile Cys Leu Ser Asp
         35                  40                  45

Glu Leu Pro Pro Gln Gly Ser Pro Val Pro Thr Gln Asp Arg Gly Thr
     50                  55                  60

Ser Thr Asp Ser Pro Cys Arg Arg Ser Ala Ala Thr Gln
 65                  70                  75
```

(2) INFORMATION FOR SEQ ID NO:18:

(i) SEQUENCE CHARACTERISTICS:
        (A) LENGTH: 68 amino acids
        (B) TYPE: amino acid
        (D) TOPOLOGY: linear (ii) MOLECULE TYPE: peptide (ix) FEATURE:
        (D) OTHER INFORMATION: JIP-1 amino acids 135-202

(xi) SEQUENCE DESCRIPTION: SEQ ID NO:18:

```
Pro Ala Pro Arg Ser Gln Gly Gln Gly Pro Gly Thr Gly Ser Gly Asp
 1               5                  10                  15

Thr Tyr Arg Pro Lys Arg Pro Thr Thr Leu Asn Leu Phe Pro Gln Val
             20                  25                  30

Pro Arg Ser Gln Asp Thr Leu Asn Asn Ser Leu Gly Lys Lys His
         35                  40                  45

Ser Trp Gln Asp Arg Val Ser Arg Ser Ser Pro Leu Lys Thr Gly
     50                  55                  60

Glu Gln Thr Pro
 65
```

(2) INFORMATION FOR SEQ ID NO:19:

(i) SEQUENCE CHARACTERISTICS:
            (A) LENGTH: 59 amino acids
            (B) TYPE: amino acid
            (D) TOPOLOGY: linear (ii) MOLECULE TYPE: peptide (ix) FEATURE:
            (D) OTHER INFORMATION: JIP-1 amino acids 144-202

(xi) SEQUENCE DESCRIPTION: SEQ ID NO:19:

Pro Gly Thr Gly Ser Gly Asp Thr Tyr Arg Pro Lys Arg Pro Thr Thr
  1               5                  10                  15

Leu Asn Leu Phe Pro Gln Val Pro Arg Ser Gln Asp Thr Leu Asn Asn
               20                  25                  30

Asn Ser Leu Gly Lys Lys His Ser Trp Gln Asp Arg Val Ser Arg Ser
           35                  40                  45

Ser Ser Pro Leu Lys Thr Gly Glu Gln Thr Pro
       50                  55

(2) INFORMATION FOR SEQ ID NO:20:

(i) SEQUENCE CHARACTERISTICS:
            (A) LENGTH: 49 amino acids
            (B) TYPE: amino acid
            (D) TOPOLOGY: linear (ii) MOLECULE TYPE: peptide (ix) FEATURE:
            (D) OTHER INFORMATION: JIP-1 amino acids 154-202

(xi) SEQUENCE DESCRIPTION: SEQ ID NO:20:

Pro Lys Arg Pro Thr Thr Leu Asn Leu Phe Pro Gln Val Pro Arg Ser
  1               5                  10                  15

Gln Asp Thr Leu Asn Asn Asn Ser Leu Gly Lys Lys His Ser Trp Gln
               20                  25                  30

Asp Arg Val Ser Arg Ser Ser Pro Leu Lys Thr Gly Glu Gln Thr
           35                  40                  45

Pro (2) INFORMATION FOR SEQ ID NO:21:

(i) SEQUENCE CHARACTERISTICS:
            (A) LENGTH: 39 amino acids
            (B) TYPE: amino acid
            (D) TOPOLOGY: linear (ii) MOLECULE TYPE: peptide (ix) FEATURE:
            (D) OTHER INFORMATION: JIP-1 amino acids 164-202

(xi) SEQUENCE DESCRIPTION: SEQ ID NO:21:

Pro Gln Val Pro Arg Ser Gln Asp Thr Leu Asn Asn Ser Leu Gly
  1               5                  10                  15

Lys Lys His Ser Trp Gln Asp Arg Val Ser Arg Ser Ser Pro Leu
               20                  25                  30

Lys Thr Gly Glu Gln Thr Pro
           35

(2) INFORMATION FOR SEQ ID NO:22:

(i) SEQUENCE CHARACTERISTICS:
            (A) LENGTH: 17 amino acids

```
        (B) TYPE: amino acid
        (D) TOPOLOGY: linear (ii) MOLECULE TYPE: peptide (ix) FEATURE:
        (D) OTHER INFORMATION: JIP-1 amino acids 127-143

(xi) SEQUENCE DESCRIPTION: SEQ ID NO:22:

Pro Lys Ala Glu Ser Asn Gln Asp Pro Ala Pro Arg Ser Gln Gly Gln
 1               5                  10                  15

Gly (2) INFORMATION FOR SEQ ID NO:23:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (D) OTHER INFORMATION: JIP-1 amino acids 127-153

(xi) SEQUENCE DESCRIPTION: SEQ ID NO:23:

Pro Lys Ala Glu Ser Asn Gln Asp Pro Ala Pro Arg Ser Gln Gly Gln
 1               5                  10                  15

Gly Pro Gly Thr Gly Ser Gly Asp Thr Tyr Arg
            20                  25

(2) INFORMATION FOR SEQ ID NO:24:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (ix) FEATURE:
        (D) OTHER INFORMATION: JIP-1 amino acids 127-163

(xi) SEQUENCE DESCRIPTION: SEQ ID NO:24:

Pro Lys Ala Glu Ser Asn Gln Asp Pro Ala Pro Arg Ser Gln Gly Gln
 1               5                  10                  15

Gly Pro Gly Thr Gly Ser Gly Asp Thr Tyr Arg Pro Lys Arg Pro Thr
            20                  25                  30

Thr Leu Asn Leu Phe
            35

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (B) LOCATION: 3...3
        (D) OTHER INFORMATION: where R at position 3 is A or G
        (B) LOCATION: 6...6
        (D) OTHER INFORMATION: where R at position 6 is A or G
        (B) LOCATION: 9...9
        (D) OTHER INFORMATION: where Y at position 9 is C or T
        (B) LOCATION: 12...12
```

(D) OTHER INFORMATION: where R at position 12 is A or G
            (B) LOCATION: 15...15
            (D) OTHER INFORMATION: where Y at position 15 is C or T
            (B) LOCATION: 18...18
            (D) OTHER INFORMATION: where R at position 18 is A or G (xi) SEQUENCE DESCRIPTION: SEQ ID NO :25:

GARGARTTYG ARGAYGARGA                                              20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (B) LOCATION: 3...3
        (D) OTHER INFORMATION: where N at position 3 is A, C, G or T
        (B) LOCATION: 6...6
        (D) OTHER INFORMATION: where R at position 6 is A or G
        (B) LOCATION: 9...9
        (D) OTHER INFORMATION: where R at position 9 is A or G
        (B) LOCATION: 12...12
        (D) OTHER INFORMATION: where Y at position 12 is C or T
        (B) LOCATION: 15...15
        (D) OTHER INFORMATION: where N at position 15 is A, C, G or T (xi) SEQUENCE DESCRIPTION: SEQ ID NO:26:

GGNAARAARC AYAGNTGGCA                                              20

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (B) LOCATION: 4...4
        (D) OTHER INFORMATION: where R at position 4 is A or G
        (B) LOCATION: 7...7
        (D) OTHER INFORMATION: where W at position 7 is A or T
        (B) LOCATION: 10...10
        (D) OTHER INFORMATION: where N at position 10 is A, C, G or T
        (B) LOCATION: 13...13
        (D) OTHER INFORMATION: where Y at position 13 is C or T
        (B) LOCATION: 16...16
        (D) OTHER INFORMATION: where W at position 16 is A or T (xi) SEQUENCE DESCRIPTION: SEQ ID NO:27:

CATRTTWTAN GCYTCWTACC A                                            21

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (B) LOCATION: 3...3
        (D) OTHER INFORMATION: where Y at position 3 is C or T
        (B) LOCATION: 6...6

```
            (D) OTHER INFORMATION: where Y at position 6 is C or T
            (B) LOCATION: 9...9
            (D) OTHER INFORMATION: where K at position 9 is G or T
            (B) LOCATION: 12...12
            (D) OTHER INFORMATION: where R at position 12 is A or G
            (B) LOCATION: 15...15
            (D) OTHER INFORMATION: where Y at position 15 is C or T
            (B) LOCATION: 18...18
            (D) OTHER INFORMATION: where Y at position 17 is C or T
            (B) LOCATION: 21...21
            (D) OTHER INFORMATION: where R at position 21 is A or G (xi) SEQUENCE DESCRIPTION: SEQ ID NO:28:

AAYTGYTTKT ARAAYTGYTG RAA                                              23

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: RNA (xi) SEQUENCE DESCRIP TION: SEQ ID NO:29:

GGUAUCGAUA AGCUUGAUAU CGCUGUCCGG AGC                                   33

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:30:

AGAGGCACUG UCCCAUCCUG GGCCUGUUUC AUG                                   33
```

INHIBITORS OF THE JNK SIGNAL TRANSDUCTION PATHWAY AND METHODS OF USE

RELATED APPLICATION INFORMATION

This application is a divisional of application Ser. No. 08/819,177, filed Apr. 28, 1997, now U.S. Pat. No. 6,043,083 which is incorporated herein by reference in its entirety.

STATEMENT AS TO FEDERALLY SPONSORED RESEARCH

This invention was made, in part, with Government support under grants CA58396 and CA65831 awarded by the National Cancer Institute. The government may have certain rights in the invention.

FIELD OF THE INVENTION

The invention relates to signal transduction inhibitors.

BACKGROUND OF THE INVENTION

The c-Jun NH2-terminal kinase (JNK) is a member of the stress-activated group of Mitogen Activated Protein kinases (MAP kinases) implicated in the control of cell growth. The JNK signal transduction pathway is activated in response to environmental stress and by the engagement of several classes of cell surface receptors, including cytokine receptors, serpentine receptors, and receptor tyrosine kinases. Whitmarsh et al., *J. Mol. Med.*, 74:589 (1996). In addition, genetic studies of Drosophila have demonstrated that JNK is required for early embryonic development. Sluss et al., *Genes & Dev.*, 10:2745 (1996); Riesgo-Escovar et al., *Genes & Dev.* 10:2759 (1996). In mammalian cells, JNK has been implicated in the immune response, oncogenic transformation, and apoptosis. JNK mediates these-effects, at least in part, by increasing the expression of target genes. Targets of the JNK signal transduction pathway include the transcription factors c-Jun, ATF2, and Elk-1. Whitmarsh et al., supra.

JNK is activated in the liver by metabolic oxidative stress. Mendelson et al., *Proc. Natl. Acad. Sci. USA* 93:12908–12913 (1996). Activation of JNK also occurs in the kidney during stress, for example, during Bchemic renal failure. Demari et al., *Am. J. Physiol.* 272:F292–F298 (1997). JNK is also activated during cardiovascular disease such as ischemia Ireperfusion and during organ transplantation. Pombo et al., *J. Biol. Chem.* 269:26546–26551 (1994); Force et al., *Circ. Res.* 78:947–53 (1996).

While JNK is located in both the cytoplasmic and the nuclear compartments of quiescent cells, activation of the JNK signal transduction pathway is associated with accumulation of JNK in the nucleus. Mechanisms governing this sub-cellular distribution have not been previously elucidated.

Anchor or tethering proteins play an important role in the regulation of multiple signal transduction pathways. These anchor proteins, which include the nuclear factor kappa B (NFkB) inhibitor IkB, the A kinase anchor protein (AKAP) group of proteins that bind the type II cyclic adenosine monophosphate (AMP) dependent protein kinase, and the p190 protein that binds $Ca^{2+}$-calmodulin-dependent protein kinase II, localize their tethered partners to specific sub-cellular compartments. Verma et al., *Genes & Dev.*, 9:2723 (1995); McNeill et al., *J. Biol. Chem.*, 270:10043 (1995); Faux et al., *Trends Biochem. Sci.*, 21:312 (1996)). Anchor proteins also target enzymes to specific substrates, and create multi-enzyme signaling complexes, such as the Ste5 MAP kinase scaffold complex and the AKAP79 kinase/phosphatase scaffold complex. Choi et al., *Cell*, 78:499 (1994); Klauck et al., *Science*, 271:1589 (1996); Faux et al., *Cell*, 85:9 (1996)).

SUMMARY OF THE INVENTION

The invention, which is based on the discovery of a cytoplasmic anchor protein, JNK-interacting protein 1 (JIP-1; SEQ ID NO:1), features JIP-1 polypeptides and nucleic acids, therapeutic compositions containing these polypeptides and nucleic acids, and methods of administering these compositions. JIP-1 specifically binds to and inhibits the biological effects of JNK, including the initiation of apoptosis and oncogenic transformation. JIP-1 is therefore useful as a therapeutic agent for treating pathological conditions characterized by apoptosis or transformation. For example, JIP-1 compositions can be used to treat neurodegenerative diseases characterized by apoptosis, including Parkinson's disease and Alzheimer's disease; and blood clots, which left untreated could result in stroke and associated memory loss. Other conditions that can be treated using the compositions and methods of the invention are autoimmune diseases such as arthritis; other conditions characterized by inflammation; and malignancies, such as leukemias, e.g., chronic myelogenous leukemia (CML). other conditions that can be treated with JIP-1 compositions include oxidative damage to organs such as the liver and kidney, and heart disease, particularly damage due to ischemia/reperfusion and cardiomyopathy. JIP-1 compositions can also be used to treat donor organs for transplantation. These organs are exposed to substantial environmental stress, the effects of which are blocked by JNK inhibitors such as JIP-1.

The invention features a substantially pure JIP-1 polypeptide. A "JIP-1 polypeptide" is a protein having an amino acid sequence that specifically binds JNK to the same extent, or at least 10% of the binding activity of wildtype JIP-1. Such polypeptides can be from 5 to 200 amino acids in length, e.g., from 10 to 100 amino acids in length, or from 20 to 50 amino acids in length. Such polypeptides include the JNK Binding Domain (JBD), or portions thereof, of JIP-1 (e.g., amino acids 148 to 174, forming the "core" of the JBD of wildtype JIP-1, shown in FIG. 2, and having the sequence SGDTYRPKRPTTLNLFPQVPRSQDTLN; SEQ ID NO:3). JIP-1 polypeptides are preferably derived from a mammal, such as a mouse or a human.

In various embodiments, the polypeptide is soluble, the polypeptide includes the JNK-binding domain of JIP-1 or a portion thereof, the polypeptide is at least 80%, 90%, or 100% identical to the amino acid sequence from amino acid 148 to amino acid 174 of JIP-1 (the core JNK-binding domain; SEQ ID NO:3), or the polypeptide has an amino acid sequence identical to the amino acid sequence from amino acid 148 to amino acid 174 of JIP-1 (SEQ ID NO:3), or the polypeptide is at least 80%, 90%, or 100% identical to the amino acid sequence from amino acid 127 to amino acid 281 of JIP-1 (the JNK-binding domain; SEQ ID NO:4).

The polypeptides of the invention can be modified to enhance their uptake by cells. Such modifications increase the hydrophobicity of molecules to facilitate passage through the lipid bilayer of the cell membrane. For example, polypeptides can be complexed with myristic acid or packaged in liposomes. Alternatively, JIP-1 polypeptides can be complexed with hydrophobic moieties (e.g., lipids) or peptides that increase the delivery of proteins into cells.

The invention also includes peptide mimetics of JIP-1 polypeptides. A "peptide mimetic" of a known polypeptide is a compound that mimics the activity of the peptide or polypeptide, but which is composed of molecules other than, or in addition to, amino acids.

By "polypeptide" is meant any chain of amino acids, regardless of length or post-translational modification (e.g., glycosylation or phosphorylation), and thus includes peptides, proteins, and fusion proteins.

A "substantially identical" polypeptide sequence differs from a given sequence only by conservative amino acid substitutions or by one or more nonconservative substitutions, deletions, or insertions located at positions which do not destroy the function of the polypeptide compared to wildtype JIP-1. Polypeptides of the invention can be 70%, 80%, 85%, 90%, or 95% identical to wildtype JIP-1.

A "substantially pure" preparation is at least 60% by weight of the compound of interest, e.g., a JIP-1 polypeptide or fragment of a JIP-1 polypeptide. Preferably the preparation is at least 75%, more preferably at least 90%, and more preferably at least 95% by weight of the compound of interest. Purity can be measured by any appropriate standard method, e.g., column chromatography, polyacrylamide gel electrophoresis, or High Pressure Liquid Chromatography (HPLC) analysis.

The polypeptides of the invention include, but are not limited to, recombinant polypeptides, natural polypeptides, and synthetic polypeptides, as well as preproteins or proproteins and biologically active fragments. A "biologically active fragment" of JIP-1 is a fragment having at least 50%, 70%, 80%, 90%, 95%, or 100% or greater, of the activity of naturally occurring or synthetic, full length JIP-1.

The polypeptides of the invention can be physically linked to another polypeptide, e.g., a marker polypeptide. For example, the polypeptide can be fused to a hexahistidine tag to facilitate purification of bacterially expressed proteins, or a hemagglutinin tag to facilitate purification of protein expressed in eukaryotic cells.

In another aspect, the invention features an isolated nucleic acid that includes a sequence encoding a JIP-1 polypeptide or a fragment of such a polypeptide. Preferably, the nucleic acid is derived from a mammal.

The invention also encompasses nucleic acids that hybridize under stringent conditions (as described herein) to a nucleic acid encoding a JIP-1 polypeptide. Stringent conditions include hybridization at 68° C. in 5×SSC/5× Denhardt's solution/1.0% SDS, or in 0.5 M $NaHPO_4$ (pH 7.2)/1 mM EDTA/7% SDS, or in 50% formamide/0.25 M $NaHPO_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM $NaHPO_4$ (pH 7.2)/1 mM EDTA/5% SDS at 50° C., or in 40 mM $NaHPO_4$ (pH 7.2) 1 mM EDTA/1% SDS at 50° C. Moderately stringent conditions include washing in 3×SSC at 42° C. The parameters of salt concentration and temperature can be varied to achieve the desired level of identity between the probe and the target nucleic acid. For guidance regarding such conditions see, e.g., Sambrook et al., *Molecular Cloning, A Laboratory Manual,* Cold Spring Harbor Press, Cold Spring Harbor, N.Y.; and Ausubel et al., supra, at Unit 2.10.

The hybridizing portion of the hybridizing nucleic acid is preferably 20, 30, 50, or 70 bases long. The hybridizing portion of the hybridizing nucleic acid can be 95% or even 98% or 100% identical to the sequence of a portion of a nucleic acid encoding a JIP-1 polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by naturally-occurring JIP-1. Thus, they may encode a protein that is shorter or longer than the various forms of JIP-1 described herein. Hybridizing nucleic acids can also encode proteins that are related to JIP-1, e.g., proteins encoded by genes that include a portion having a relatively high degree of identity to a JIP-1 gene described herein.

The term "nucleic acid" encompasses both RNA and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand.

An "isolated nucleic acid" is a nucleic acid that is free of the nucleic acids that normally flank it in the genome. The term therefore includes, e.g., a recombinant nucleic acid incorporated into a vector, such as an autonomously replicating plasmid or virus; a cDNA or genomic DNA fragment produced by polymerase chain reaction (PCR) or restriction endonuclease treatment; and recombinant DNA which is part of a hybrid gene encoding additional polypeptide sequences.

A "substantially identical" nucleic acid is a nucleic acid with a sequence that is at least 50%, preferably 70%, and more preferably 85%, 90%, or 95% homologous to a given nucleic acid sequence, e.g., SEQ ID NO:2.

The invention also features transformed cells harboring a nucleic acid encompassed by the invention. Vectors and plasmids that include a nucleic acid properly positioned for expression are also within the invention. A "transformed cell" is a cell into which (or into an ancestor of which) has been introduced, by means of recombinant DNA techniques, a DNA molecule encoding a JIP-1 polypeptide.

"Operably linked" means that the selected DNA molecule is positioned adjacent to one or more sequence elements that direct transcription and/or translation of the sequence such that the sequence elements can control transcription and/or translation of the selected DNA (i.e., the selected DNA is operably associated with the sequence elements). Such operably associated elements can be used to facilitate the production of a JIP-1 polypeptide.

The invention also features purified antibodies which specifically bind a JIP-1 protein or polypeptide. A "purified antibody" is an antibody which is at least 60%, by dry weight, free from the proteins and naturally-occurring organic molecules with which it is naturally associated. The preparation can be at least 75%, at least 90%, and up to 99% or more, by dry weight, antibody.

An antibody that "specifically binds" an antigen recognizes and binds to that antigen, e.g., a JIP-1 polypeptide.

Also within the invention are antisense molecules and ribozymes for inhibiting JIP-1 expression.

The invention also features antagonists and agonists of JIP-1. Antagonists can inhibit one or more of the functions of JIP-1. Suitable antagonists can include large or small molecules, antibodies to JIP-1, and JIP-1 polypeptides that compete with a native form of JIP-1. Such antagonists include SEQ ID NO:3, a component of an active site of JIP-1, i.e., the JNK-binding domain. Agonists of JIP-1 will enhance or facilitate one or more of the functions of JIP-1. Agonists and Antagonists include polyproline motifs, which bind to SH3 domains such as that found in JIP-1.

A "therapeutically effective amount" of a substance is an amount capable of producing a medically desirable result in a treated patient, e.g., inhibition of the expression or activity of a specific protein.

Unless otherwise defined, all technical and scientific terms used herein have the same meaning as commonly understood by one of ordinary skill in the arts of protein chemistry or molecular biology. Although methods and materials similar or equivalent to those described herein can be used in the practice or testing of the present invention, suitable methods and materials are described infra. All publications, patent applications, patents and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the detailed description and the claims.

BRIEF DESCRIPTION OF THE DRAWINGS

FIG. 1A is a schematic diagram showing the structure of a murine JIP-1 polypeptide.

FIG. 1B is a representation of the amino acid sequence of a murine JIP-1 polypeptide (SEQ ID NO:1), presented in single letter code.

FIG. 1C is a representation of the nucleotide sequence of a murine JIP-1 cDNA (SEQ ID NO:2).

FIG. 2 is a diagram showing an alignment of the JBDs (JNK-binding domains) of JIP-1 (SEQ ID NO:3), c-Jun (SEQ ID NO:5), and ATF2 (SEQ ID NO:6).

FIG. 3 is a diagram showing the amino acid sequences of wild type and mutant JIP-1 peptides (SEQ ID NOs:3 and 7 to 11), as well as a control peptide (SEQ ID NO:12).

DETAILED DESCRIPTION

Figure 4A:
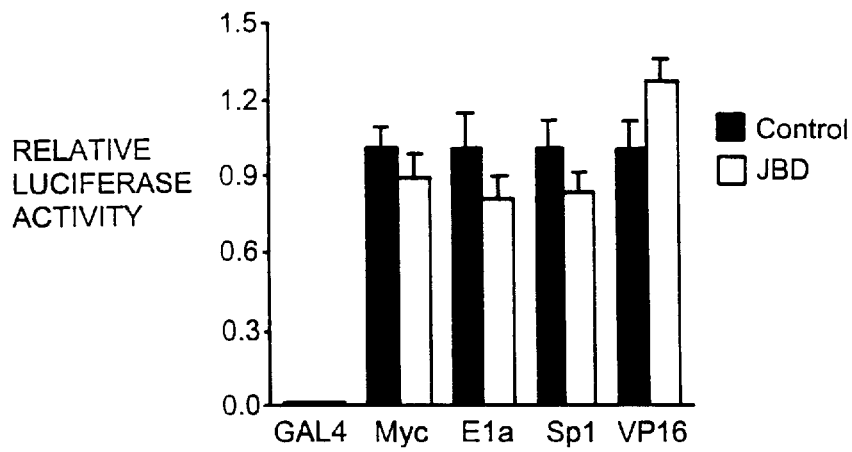
FIG. 4A is a bar graph showing the effect of recombinant JBD (JIP-1 residues 127–281) on reporter gene expression mediated by the GAL4 binding domain and GAL4 fusions with the c-myc, Sp1, and VP16 activation domains.

The invention is based on the molecular cloning and characterization of JIP-1, a cytoplasmic protein that specifically binds JNK. JIP-1 polypeptides cause cytoplasmic retention of JNK and inhibition of JNK-regulated gene expression. In addition, JIP-1 polypeptides suppress the effects of the JNK signaling pathway, including oncogenic transformation and apoptosis. These findings have important implications for the treatment or prevention of pathological conditions and diseases, many of which are characterized by transformation or apoptosis. Conditions associated with apoptosis include neurodegenerative conditions, such as Parkinson's disease or Alzheimer's disease; and blood clots, which left untreated could result in stroke and associated memory loss. Other conditions that can be treated using the compositions and methods of the invention are autoimmune diseases such as arthritis; other conditions characterized by inflammation; and malignancies, such as leukemias, e.g., chronic myelogenous leukemia (CML). JIP-1 polypeptide compositions can also be used to treat oxidative damage to organs such as the liver and kidney. Heart disease can also be treated with the compositions of the invention. Donor organs for transplantation can also be treated with JIP-1 compositions.

JIP-1 Proteins and Polypeptides

As shown in FIG. 1, the 660 amino acid JIP-1 protein has an SH3 domain at its carboxy terminal end, at amino acid positions 491–540, and a JNK-binding domain (JBD) at its amino terminal end, at amino acid positions 127–281 (SEQ ID NO:4). The core of the JBD is amino acids 148–174 (SEQ ID NO:3). The JBD of JIP-1 shares conserved residues with the JNK-binding regions of the transcription factors c-Jun and ATF2, as shown in FIG. 2.

JIP-1 polypeptides can be prepared for a wide range of uses including, but not limited to, generation of antibodies, preparation of reagents for diagnostic assays, identification of other molecules involved in transformation or apoptosis, preparation of reagents for use in screening assays for modulators of apoptosis or transformation, and preparation of therapeutic agents for treatment of disorders related to apoptosis or transformation.

The invention encompasses, but is not limited to, JIP-1 polypeptides that are functionally related to JIP-1 encoded by the nucleotide sequence of FIG. 1C (SEQ ID NO:2). Functionally related polypeptides include any polypeptide sharing a functional characteristic with wildtype JIP-1 protein, e.g., the ability to bind JNK polypeptides or to affect proliferation or apoptosis. Such functionally related JIP-1 polypeptides include, but are not limited to, polypeptides having additions or substitutions of amino acid residues within the amino acid sequence encoded by the JIP-1 sequences described herein which result in a silent change, thus producing a functionally equivalent gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to JIP-1 DNA (using random mutagenesis techniques well known to those skilled in the art) and the resulting mutant JIP-1 proteins can be tested for activity, site-directed mutations of the JIP-1 coding sequence can be engineered (using site-directed mutagenesis techniques well known to those skilled in the art) to generate mutant JIP-1 proteins with increased function, e.g., greater JNK-1 binding and inhibition of transformation.

To design functionally related and functionally variant JIP-1 polypeptides, it is useful to distinguish between conserved positions and variable positions. To preserve JIP-1 function, it is preferable that conserved residues are not altered. Moreover, alteration of non-conserved residues are preferably conservative alterations, e.g., a basic amino acid is replaced by a different basic amino acid. To produce altered function variants, it is preferable to make nonconservative changes at variable and/or conserved positions. Deletions at conserved and variable positions can also be used to create altered function variants. Conserved amino acids in JIP-1 include, but are not limited to, Lys-155, Thr-159, Leu-160, Asn-161, and Leu-162.

Preferred JIP-1 polypeptides are those that bind JNK and inhibit transformation or apoptosis. These JIP-1 polypeptides have 20%, 40%, 50%, 75%, 80%, 90%, or even greater than 100% of the activity of the full-length JIP-1 described herein. Such comparisons are generally based on equal concentrations of the molecules being compared. The comparison can also be based on the amount of protein or polypeptide required to reach 50% of the maximal stimulation obtainable.

Polypeptides corresponding to one or more domains of JIP-1, e.g., the JNK Binding Domain (JBD), are also within the scope of the invention. Preferred polypeptides are those which are soluble under normal physiological conditions. Also within the invention are fusion proteins in which a portion (e.g., one or more domains) of JIP-1 is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of JIP-1 is joined in-frame to a nucleotide sequence encoding the fusion partner. Fusion partners include, but are not limited to, the constant region of an immunoglobulin (IgFc). A fusion protein in which a JIP-1 polypeptide is fused to IgFc can be more stable and have a longer half-life in the body than the JIP-1 polypeptide on its own.

Also within the scope of the invention are various soluble forms of JIP-1, including JIP-1 expressed on its own or fused to a solubilization partner, e.g., an immunoglobulin.

In general, JIP-1 polypeptides can be produced by transformation (transfection, transduction, or infection) of a host cell with all or part of a JIP-1-encoding DNA fragment (e.g., the cDNA described herein) in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; LaJolla, Calif.).

Any of a wide variety of expression systems can be used to provide the recombinant proteins. The precise host cell used is not critical to the invention. The JIP-1 protein can be produced in a prokaryotic host (e.g., *E. coli* or *B. subtilis*) or in a eukaryotic host, e.g., yeast, such as Saccharomyces or Pichia; mammalian cells, such as COS, NIH 3T3, CHO, BHK, 293, or HeLa cells; or insect cells.

JIP-1 polypeptides can also be produced by plant cells. Viral expression vectors (e.g., cauliflower mosaic virus and tobacco mosaic virus) and plasmid expression vectors (e.g., Ti plasmid) are suitable for use in plant cells. Plant cells are available from a wide range of sources, e.g., the American Type Culture Collection, Rockland, Md. See also, e.g., Ausubel et al., *Current Protocols in Molecular Biology*, John Wiley & Sons, New York, 1995. The methods of transformation or transfection and the choice of expression vehicle will depend on the host system selected. Transformation and transfection methods are described in, e.g., Ausubel et al., supra; expression vehicles may be chosen from those described in, e.g., *Cloning Vectors: A Laboratory Manual*, P. H. Pouwels et al., 1985, Supp. 1987.

The host cells harboring the expression vehicle can be cultured in conventional nutrient media adapted as needed for activation of a chosen gene, repression of a chosen gene, selection of transformants, or amplification of a chosen gene.

A suitable expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a JIP-1 in protein would be inserted into the pMAMneo vector in an orientation designed to allow expression. The recombinant JIP-1 protein would be isolated as described below. Other preferable host cells that can be used in conjunction with the pMAMneo expression vehicle include COS cells and CHO cells (ATCC Accession Nos. CRL 1650 and CCL 61, respectively).

JIP-1 polypeptides can be expressed as fusion proteins. For example, the expression vector pUR278 can be used to create lacZ fusion proteins. See Ruther et al., *EMBO J.* 2:1791 (1983). The pGEX vectors can be used to express foreign polypeptides as fusion proteins with glutathione S-transferase (GST). In general, such fusion proteins are soluble and can be easily purified from cell lysates by adsorption to glutathione-agarose beads followed by elution in the presence of free glutathione. The pGEX vectors are designed to include thrombin or factor Xa protease cleavage sites so that the cloned target gene product can be released from the GST moiety.

In an insect cell expression system, *Autographa californica* nuclear polyhidrosis virus (AcNPV), which grows in *Spodoptera frugiperda* cells, is used as a vector to express foreign genes. A JIP-1 coding sequence can be cloned individually into non-essential regions (for example the polyhedrin gene) of the virus and placed under control of a AcNPV promoter, e.g., the polyhedrin promoter. Successful insertion of a gene encoding a JIP-1 polypeptide or protein will result in inactivation of the polyhedrin gene and production of non-occluded recombinant virus (i.e., virus lacking the proteinaceous coat encoded by the polyhedrin gene). *Spodoptera frugiperda* cells are then infected with these viruses, and the inserted gene is expressed. See, e.g., Smith et al., *J. Virol.* 46:584 (1983); Smith, U.S. Pat. No. 4,215, 051.

In mammalian host cells, a number of viral-based expression systems can be utilized. In cases where an adenovirus is used as an expression vector, the JIP-1 nucleic acid sequence can be ligated to an adenovirus transcription/translation control complex, e.g., the late promoter and tripartite leader sequence, to form a chimeric gene. This chimeric gene can then be inserted into the adenovirus genome by in vitro or in vivo recombination. Insertion into a non-essential region of the viral genome (e.g., the E1 or E3 gene) will result in a recombinant virus that is viable and capable of expressing a JIP-1 gene product in infected hosts. See, e.g., Logan, *Proc. Natl. Acad. Sci. USA,* 81:3655 (1984).

Specific initiation signals may be required for efficient translation of inserted nucleic acid sequences. These signals include the ATG initiation codon and adjacent sequences. In cases where an entire native JIP-1 gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. Exogenous translational control signals and initiation codons can be of a variety of origins, both natural and synthetic. The efficiency of expression may be enhanced by the inclusion of appropriate transcription enhancer elements. Bittner et al., *Methods in Enzymol.,* 153:516 (1987).

In addition, a host cell may be chosen which modulates the expression of the inserted sequences, or modifies and processes the gene product in a desired fashion. Such modifications (e.g., glycosylation) and processing (e.g., cleavage) of protein products may be important for the function of the protein. Different host cells have characteristic and specific mechanisms for post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and WI38 cells.

Alternatively, a JIP-1 protein can be produced by a stably-transfected mammalian cell line. A number of vectors suitable for stable transfection of mammalian cells are available to the public. See, e.g., Pouwels et al., supra. Methods for constructing such cell lines are also publicly available. See, e.g., Ausubel et al., supra. JIP-1 cDNA can be cloned into an expression vector that includes the dihydrofolate reductase (DHFR) gene. Methotrexate (0.01–300 $\mu$M) is present in the culture medium to select for cells which have integrated the plasmid and, therefore, the JIP-1 cDNA. See Ausubel et al., supra. This dominant selection can be accomplished in most cell types.

Recombinant protein expression can be increased by DHFR-mediated amplification of the transfected gene. Methods for selecting cell lines bearing gene amplifications are described in Ausubel et al., supra. Such methods generally involve extended culture in medium containing gradually increasing levels of methotrexate. DHFR-containing expression vectors commonly used for this purpose include pCVSEII-DHFR and pAdD26SV(A). See Ausubel et al., supra. Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyltransferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA,* 78:2072 (1981); neo, which confers resistance to the aminoglycoside G-418 (Colberre-Garapin et al., *J. Mol. Biol.,* 150:1 (1981)); and hygro, which confers resistance to hygromycin (Santerre et al., *Gene,* 30:147 (1981)), can be used.

Alternatively, any fusion protein can be readily purified by utilizing an antibody specific for the fusion protein being expressed. For example, a system described in Janknecht et al., *Proc. Natl. Acad. Sci. USA,* 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns, and histidine-tagged proteins are selectively eluted with imidazole-containing buffers.

Alternatively, JIP-1 or a portion thereof can be fused to an immunoglobulin Fc domain. Such a fusion protein can be readily purified using a protein A column. Moreover, such fusion proteins permit the production of a dimeric form of a JIP-1 polypeptide having increased stability in vivo.

After the recombinant JIP-1 protein is expressed, it is isolated. Secreted forms can be isolated from the culture media, while non-secreted forms must be isolated from the host cells. Proteins can be isolated by affinity chromatography. An anti-JIP-1 antibody (e.g., produced as described herein) is attached to a column and used to isolate the JIP-1 protein. Lysis and fractionation of JIP-1 protein-harboring cells prior to affinity chromatography can be performed by standard methods. See, e.g., Ausubel et al., supra. Alternatively, a JIP-1 fusion protein, for example, a JIP-1-maltose binding protein, a JIP-1-$\beta$-galactosidase, or a JIP-1-trpE fusion protein, can be constructed and used for JIP-1 protein isolation. See, e.g., Ausubel et al., supra; New England Biolabs, Beverly, Mass.

Once isolated, the recombinant protein can, if desired, be further purified, e.g., by high performance liquid chromatography using standard techniques. See, e.g., Fisher, *Laboratory Techniques In Biochemistry And Molecular Biology,* Work et al., eds., Elsevier (1980).

Polypeptides of the invention, particularly short JIP-1 fragments, can also be produced by chemical synthesis, e.g., by the methods described in *Solid Phase Peptide Synthesis,* 2nd ed., The Pierce Chemical Co., Rockford, Ill., 1984.

The invention also features proteins which interact with JIP-1 and which are involved in the function of JIP-1. Also included in the invention are the genes encoding these interacting proteins. Interacting proteins can be identified using methods known to those skilled in the art. One method suitable method is the "two-hybrid system" which detects protein interactions in vivo. See, e.g., Chien et al., *Proc. Natl. Acad. Sci. USA,* 88:9578 (1991). A kit for practicing this method is available from Clontech (Palo Alto, Calif.).

JIP-1 Nucleic Acids

The JIP-1 cDNA sequences described herein, and related family members of the JIP-1 gene present in mouse, human, or other species can be identified and readily isolated without undue experimentation by well known molecular biological techniques given the specific sequences described herein. Further, genes may exist at other loci that encode proteins having extensive homology to JIP-1 polypeptides or one or more domains of JIP-1 polypeptides. These genes can be identified by known techniques using the sequences disclosed herein. For example, hybridization of JIP-1 probes to homologous nucleic acids is performed under stringent conditions. Alternatively, a labeled fragment can be used to screen a genomic library derived from the organism of interest, again, using appropriately stringent conditions. Such stringent conditions are well known, and will vary predictably depending on the specific organisms from which the library and the labeled sequences are derived.

Nucleic acid duplex or hybrid stability is expressed as the melting temperature, or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of SSC or SSPE. It is then assumed that 1% mismatching results in a 1° C. decrease in the $T_m$, and the temperature of the final wash is reduced accordingly (for example, if sequences with ≧95% identity with the probe are sought, the final wash temperature is decreased by 5° C.). Note that this assumption is very approximate, and the actual change in $T_m$ can be between 0.5° and 1.50° C. per 1% mismatch.

As used herein, stringent conditions include hybridization at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the desired level of identity between the probe and the target nucleic acid. For guidance regarding such conditions see, e.g., Sambrook et al., *Molecular Cloning, A Laboratory Manual*, Cold Spring Harbor Press, Cold Spring Harbor, N.Y.; and Ausubel et al., supra, at Unit 2.10.

Upon detection of JIP-1 transcript in human cell lines by Northern blot analysis, cDNA libraries can be constructed from RNA isolated from these cell lines utilizing standard techniques. The human cDNA library can then be screened with a JIP-1 probe to isolate a human JIP-1 cDNA.

Alternatively, a human genomic DNA library can be screened using JIP-1 probes. Hybridizing clones can be sequenced and the intron and exon structure of the human JIP-1 gene can be elucidated. Once a genomic sequence is obtained, oligonucleotide primers can be designed based on the sequence for use in Reverse Transcriptase-coupled PCR, e.g., to isolate human JIP-1 cDNA. An example of a suitable probe for screening a human genomic library is the coding region (nucleotides 180 to 2159) of the mouse JIP-1 cDNA (SEQ ID NO:2).

Further, a previously unknown gene sequence can be isolated by performing PCR using two degenerate oligonucleotide primer pools designed on the basis of nucleotide sequences within the JIP-1 cDNA defined herein. Degenerate PCR primers that can be used include:

5' GARGARTTYGARGAYGARGA 3' (sense; SEQ ID NO:25);
5' GGNAARAARCAYAGNTGGCA 3' (sense; SEQ ID NO:26);
5' CATRTTWTANGCYTCWTACCA 3' (antisense; SEQ ID NO:27); and
5' AAYTGYTTKTARAAYTGYTGRAA 3' (antisense; SEQ ID NO:28), where W is A or T, K is G or T, R is A or G, Y is C or T, and N is A, C, G or T. The template for the reaction can be cDNA obtained by reverse transcription of mRNA prepared from human or non-human cell lines or tissue known to express, or suspected of expressing, JIP-1. The PCR product can be subcloned and sequenced to insure that the amplified sequences represent the sequences of JIP-1 or JIP-1-like gene nucleic acid sequences.

The PCR fragment can then be used to isolate a full length cDNA clone by a variety of methods. For example, the amplified fragment can be labeled and used to screen a cDNA library in bacteriophage. Alternatively, the labeled fragment can be used to screen a genomic library.

PCR technology also can be used to isolate full length cDNA sequences. For example, RNA can be isolated, following standard procedures, from an appropriate tissue or cell line. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction. After digestion with RNAase H, and second strand synthesis can be primed with a poly-C primer. Thus, cDNA sequences upstream of the amplified fragment can easily be isolated. For a review of useful cloning strategies, see e.g., Sambrook et al., supra; Ausubel et al., supra.

Mutant cDNAs can also be isolated using PCR techniques. The first cDNA strand can be synthesized by hybridizing an oligo-dT oligonucleotide to mRNA isolated from tissue known to be or suspected of being expressed in an individual putatively carrying the mutant allele, and by extending the new strand with reverse transcriptase. The second strand of the cDNA can then be synthesized using an oligonucleotide that hybridizes specifically to the 5'—end of the normal gene. Using these two oligonucleotides as primers, the product is amplified via PCR, cloned into a suitable vector, and subjected to DNA sequence analysis by methods well known in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to express, or suspected of expressing, the gene of interest in an individual suspected of carrying or known to carry the mutant allele. The normal gene or any suitable fragment thereof can then be labeled and used as a probe to identify the corresponding mutant allele in the library. The clone containing the mutant gene can then be purified through methods routinely practiced in the art, and subjected to sequence analysis using standard techniques as described herein.

Additionally, an expression library can be constructed using DNA isolated from or cDNA synthesized from a tissue known to express or suspected of expressing the gene of interest in an individual suspected of carrying or known to carry the mutant allele. In this manner, gene products made by this tissue can be expressed and screened using standard antibody screening techniques in conjunction with antibodies raised against the normal gene product, as described herein. For screening techniques, see, for example, Harlow et al., eds., *Antibodies: A Laboratory Manual*, Cold Spring Harbor Press, Cold Spring Harbor, N.Y. (1988).

In cases where the mutation results in an expressed gene product with altered function (e.g., as a result of a missense mutation), a polyclonal set of antibodies is likely to cross-react with the mutant gene product. Library clones detected via their reaction with such labeled antibodies can be purified and subjected to sequence analysis as described herein.

JIP-1 Peptide Mimetics

JIP-1 peptide mimetics can be constructed by structure-based drug design through replacement of amino acids by organic moieties. See, e.g., Hughes, *Philos. Trans. R. Soc. Lond.*, 290:387–394 (1980); Hodgson, *Biotechnol.*, 9:19–21 (1991); Suckling, *Sci. Prog.*, 75:323–359 (1991). The use of peptide mimetics can be enhanced through the use of combinatorial chemistry to create drug libraries. The design of peptide mimetics can be aided by identifying amino acid mutations that increase or decrease JIP-1 binding to JNK.

Approaches that can be used include the yeast two hybrid method (see, e.g., Chien et al., *Proc. Natl. Acad. Sci. USA,* 88:9578 (1991); kit from Clontech, Palo Alto, Calif.), and the phage display method. The two hybrid method detects protein-protein interactions in yeast. Fields et al., *Nature,* 340:245–246 (1989). The phage display method detects the interaction between an immobilized protein and a protein that is expressed on the surface of phages (e.g. lambda and M13). Amberg, et al., *Strategies,* 6:2–4 (1993); Hogrefe et al., *Gene,* 128:119–126 (1993). These methods allow positive and negative selection for protein-protein interactions and the identification of the sequences that determine these interations.

Transgenic Animals

JIP-1 polypeptides can also be expressed in transgenic animals. Animals of any species, including, but not limited to, mice, rats, rabbits, guinea pigs, pigs, micro-pigs, goats, and non-human primates, e.g., baboons, monkeys, and chimpanzees, can be used to generate JIP-1-expressing transgenic animals.

Various techniques known in the art can be used to introduce a JIP-1 transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci. USA,* 82:6148 (1985)); gene targeting into embryonic stem cells (Thompson et al., *Cell,* 56:313 (1989)); and electroporation of embryos (Lo, *Mol. Cell. Biol,* 3:1803 (1983)).

The present invention provides for transgenic animals that carry the JIP-1 transgene in all their cells, as well as animals that carry the transgene in some, but not all of their cells, i.e., mosaic animals. The transgene can be integrated as a single transgene or in concatamers, e.g., head-to-head tandems or head-to-tail tandems. The transgene can also be selectively introduced into and activated in a particular cell type. Lasko et al., *Proc. Natl. Acad. Sci. USA,* 89:6232 (1992). The regulatory sequences required for such a cell-type specific activation will depend upon the particular cell type of interest, and will be apparent to those of skill in the art.

When it is desired that the JIP-1 transgene be integrated into the chromosomal site of the endogenous JIP-1 gene, gene targeting is preferred. Vectors containing some nucleotide sequences homologous to an endogenous JIP-1 gene are designed for the purpose of integrating via homologous recombination into the endogenous gene and disrupting its function. The transgene also can be selectively introduced into a particular cell type, thus inactivating the endogenous JIP-1 gene in only that cell type. See Gu et al., *Science,* 265:103 (1984). The regulatory sequences required for such a cell-type specific inactivation will depend upon the particular cell type of interest, and will be apparent to those of skill in the art.

Once transgenic animals have been generated, the expression of the recombinant JIP-1 gene can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-PCR. Samples of tissues expressing JIP-1 can also be evaluated immunocytochemically using antibodies specific for the JIP-1 transgene product.

Anti-JIP-1 Antibodies

Since JIP-1 is an inhibitor of JNK, inhibition of JIP-1 increases JNK activity. Increased JNK expression results in increased apoptosis, e.g., in neurons. Induction of apoptosis would be desirable in brain tumors, for example. Therefore, antibodies specific for JIP-1 can be used to inhibit JIP-1 expression.

Human JIP-1 proteins and polypeptides (or immunogenic fragments or analogs) can be used to raise antibodies; such polypeptides can be produced by recombinant or peptide synthetic techniques. See, e.g., *Solid Phase Peptide Synthesis,* supra; Ausubel et al., supra. In general, the peptides can be coupled to a carrier protein, such as KLH, mixed with an adjuvant, and injected into a host mammal. Antibodies can be purified by peptide antigen affinity chromatography.

In particular, various host animals can be immunized by injection with a JIP-1 protein or polypeptide. Host animals include rabbits, mice, guinea pigs, and rats. Various adjuvants can be used to increase the immunological response, depending on the host species, including but not limited to Freund's (complete or incomplete); mineral gels, such as aluminum hydroxide; surface active substances such as lysolecithin; pluronic polyols; polyanions; peptides; oil emulsions; keyhole limpet hemocyanin; dinitrophenol; and potentially useful human adjuvants such as BCG (bacillus Calmette-Guerin) and Corynebacterium parvum. Polyclonal antibodies are heterogeneous populations of antibody molecules derived from the sera of the immunized animals.

The invention includes monoclonal antibodies, polyclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the JIP-1 polypeptides described above and standard hybridoma technology. See, e.g., Kohler et al., *Nature,* 256:495 (1975); Kohler et al., *Eur. J. Immunol.,* 6:511 (1976); Kohler et al., *Eur. J. Immunol.,* 6:292 (1976); Hammerling et al., In *Monoclonal Antibodies and T Cell Hybridomas,* Elsevier, N.Y. (1981); Ausubel et al., supra.

In particular, monoclonal antibodies can be obtained by any technique that provides for the production of antibody molecules by continuous cell lines in culture. Such methods include those described in Kohler et al., *Nature* 256:495 (1975), and U.S. Pat. No. 4,376,110. Other methods of producing monoclonal antibodies include the human B-cell hybridoma technique (Kozbor et al., *Immunology Today* 4:72 (1983); Cole et al., *Proc. Natl. Acad. Sci. USA* 80:2026 (1983), and the EBV-hybridoma technique (Cole et al., *Monoclonal Antibodies and Cancer Therapy,* Alan R. Liss, Inc., pp. 77–96 (1983)). Such antibodies can be of any immunoglobulin class, e.g., IgG, IgM, IgE, IgA, IgD, and any subclass thereof. Hybridomas producing the monoclonal antibodies of the invention may be cultivated in vitro or in vivo. The ability to produce high titers of monoclonal antibodies in vivo makes this the presently preferred method of production.

Polyclonal or monoclonal antibodies are tested for specific JIP-1 recognition by Western blot or immunoprecipitation analysis by standard methods. See, e.g., Ausubel et al., supra. Antibodies that specifically recognize and bind to JIP-1 are useful in the invention. These antibodies can be used in immunoassays to monitor the level of JIP-1 produced by a mammal, e.g., to determine the amount or subcellular location of JIP-1).

Preferably, antibodies of the invention are produced using JIP-1 polypeptides that correspond to regions of the JIP-1 protein that lie outside highly conserved regions and appear likely to be antigenic, by criteria such as high frequency of charged residues. Such fragments can be generated by standard PCR techniques and then cloned into the pGEX expression vector. Ausubel et al., supra. Fusion proteins are expressed in E. coli and purified using a glutathione agarose affinity matrix as described in Ausubel, et al., supra.

In some cases it may be desirable to minimize the potential problems of low affinity or specificity of antisera. In such circumstances, two or three fusion proteins can be generated for each protein, and each fusion protein can be injected into at least two rabbits. Antisera can be raised by injections in a series, preferably including at least three booster injections.

Antisera is also checked for its ability to immunoprecipitate recombinant JIP-1 proteins or control proteins, such as glucocorticoid receptor, CAT, or luciferase.

The antibodies can be used to detect JIP-1 in a biological sample as part of a diagnostic assay. Antibodies also can be used in a screening assay to measure the effect of a candidate compound on expression or localization of JIP-1. Additionally, such antibodies can be used in conjunction with the gene therapy techniques, e.g., to evaluate the normal and/or engineered JIP-1-expressing cells prior to their introduction into the patient. Such antibodies additionally can be used in a method for inhibiting abnormal JIP-1 activity. Such abnormal activity includes altered apoptosis and proliferation, resulting in neurodegenerative diseases, autoimmune disease, cancers such as leukemias. Other abnormal JIP-1 activity includes damage caused by ischemia/reperfusion, especially in heart disease, kidney damage, and stroke.

For theraputic uses, murine or other monoclonal antibodies should be altered to make them less immunogenic when administered to human patients. For example, techniques have been developed for the production of "chimeric antibodies." See Morrison et al., *Proc. Natl. Acad. Sci.*, 81:6851 (1984); Neuberger et al., *Nature,* 312:604 (1984); Takeda et al., *Nature,* 314:452 (1984). These techniques involve splicing the genes from a mouse antibody molecule of appropriate antigen specificity together with genes from a human antibody of appropriate biological activity. Such chimeric antibodies have, e.g., a variable region derived from a murine antibody and a constant region derived from a human antibody.

Alternatively, single chain antibodies specific for JIP-1 polypeptides can be produced using known techniques. See, e.g., U.S. Pat. Nos. 4,946,778 and 4,704,692. Single chain antibodies are formed by linking the heavy and light chain fragments of the Fv region via an amino acid bridge, resulting in a single chain polypeptide.

Antibody fragments that recognize and bind to specific epitopes of JIP-1 can also be generated by known techniques. Such fragments include, but are not limited to, F(ab')$_2$ fragments, produced by pepsin digestion of antibody molecules, and Fab fragments, generated by reduction of the disulfide bonds of F(ab')$_2$ fragments. Alternatively, Fab expression libraries can be constructed to allow rapid and easy identification of monoclonal Fab fragments with a desired specificity. See, e.g., Huse et al., *Science* 246:1275 (1989).

Antibodies to JIP-1 can be used to generate anti-idiotypic antibodies that resemble a portion of JIP-1, using techniques well known to those skilled in the art. See, e.g., Greenspan et al., *FASEB J.* 7:437 (1993); Nisonoff, *J. Immunol.* 147:2429 (1991). For example, antibodies that bind to JIP-1 and competitively inhibit binding of other ligands can be used to generate anti-idiotypic antibodies resembling a ligand binding domain of JIP-1. These anti-idiotypic antibodies can bind and neutralize JIP-1 ligands. JIP-1 ligands include proline-rich regions of proteins, since JIP-1 has an SH3 domain that binds to these regions. There are ten isoforms of JNK. Gupta et al., *EMBO J.* 15:2760–2770 (1996). Each of these JNK isoforms is a JIP-1 ligand. Other kinases, which may be related to JNK, may also interact with JIP-1. Neutralizing anti-idiotypic antibodies or Fab fragments of anti-idiotypic antibodies can be used in therapeutic regimens.

Antisense Nucleic Acids

In alternate embodiments, therapies can be designed to reduce the level of endogenous JIP-1 gene expression, e.g., using antisense or ribozyme approaches to inhibit or prevent translation of JIP-1 mRNA transcripts; triple helix approaches to inhibit transcription of the JIP-1 gene; or targeted homologous recombination to inactivate or "knock out" the JIP-1 gene or its endogenous promoter. Delivery techniques can be designed to allow theraputic compositions to cross the blood-brain barrier (see, e.g., PCT WO89/10134).

Antisense approaches involve the design of oligonucleotides (either DNA or RNA) that are complementary to JIP-1 mRNA and inhibit expression of JIP-1 protein. Absolute complementarity of the antisense oligonucleotide to JIP-1, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation condon, should work most efficiently at inhibiting translation. However, sequences complementary to the 3' untranslated sequences of mRNAs have been shown to be effective at inhibiting translation of mRNAs as well (Wagner, *Nature,* 372:333, 1994). Thus, oligonucleotides complementary to either the 5'- or 3'-nontranslated, non-coding regions of the JIP-1 gene can be used in an antisense approach to inhibit translation of endogenous JIP-1 mRNA. Oligonucleotides complementary to the 5' region overlapping the initiation codon can be used for this purpose. Antisense oligonucleotides that are complementary to the coding region can also be used. In designing suitable oligonucleotides, target regions are generally those lacking predicted secondary structure.

Antisense oligonucleotides complementary to mRNA coding regions can also be used in accordance with the invention. Whether designed to hybridize to the 5', 3', or coding region of JIP-1 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides in length.

It is preferred that in vitro studies are first performed to quantitate the ability of the antisense oligonucleotide to inhibit gene expression. These studies preferably utilize controls that distinguish between antisense inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. Stability of the oligonucleotide can be improved by modification of the phosphodiester moieties by replacement with phosphorothioate, —CH2—, or —NH— groups. The oligonucleotides can also be stabilized by blocking the 5' and 3' termini with phosphorothioate, —CH2— or —NH— groups. Each of these modifications will lead to increased stability (e.g. by increasing modifications will lead to increased stability (e.g. by increasing resistance to nucleases) and therefore increased hybridization. The oligonucleotide can be modified at the base moiety, sugar moiety, or phosphate backbone. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA*, 86:6553 (1989); Lemaitre et al., *Proc. Natl. Acad. Sci. USA*, 84:648 (1987)); PCT Publication No. WO 88/09810) or the blood-brain barrier (see, e.g., PCT Publication No. WO 89/10134), or hybridization-triggered cleavage agents (see, e.g., Krol et al., *BioTechniques* 6:958 (1988)), or intercalating agents (see e.g., Zon, *Pharm. Res.* 5:539 (1988)). To this end, the oligonucleotide can be conjugated to another molecule, e.g., a peptide, hybridization triggered cross-linking agent, transport agent, or hybridization-triggered cleavage agent.

The antisense oligonucleotide can include at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl)uracil, (acp3)w, and 2,6-diaminopurine.

The antisense oligonucleotide can also include at least one modified sugar moiety selected from the group including, but not limited to, arabinose, 2-fluoroarabinose, xylulose, and hexose.

In yet another embodiment, the antisense oligonucleotide includes at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an á-anomeric oligonucleotide. An á-anomeric oligonucleotide forms specific double-stranded hybrids with complementary RNA in which, contrary to the usual â-units, the strands run parallel to each other (Gautier et al., *Nucl. Acids. Res.*, 15:6625 (1987)). The oligonucleotide is a 2'-0-methylribonucleotide (Inoue et al., *Nucl. Acids Res.*, 15:6131 (1987)), or a chimeric RNA-DNA analog (Inoue et al., *FEBS Lett.*, 215:327 (1987)).

Antisense oligonucleotides of the invention can be synthesized by. standard methods known in the art, e.g., by use of an automated DNA synthesizer (commercially available from Biosearch, Applied Biosystems, etc.). As examples, phosphorothioate oligonucleotides can be synthesized by the method of Stein et al. (*Nucl. Acids Res.*, 16:3209 (1988)), and methylphosphonate oligonucleotides can be prepared by use of controlled pore glass polymer supports (Sarin et al., *Proc. Natl. Acad. Sci. USA*, 85:7448 (1988)).

The antisense molecules should be delivered to cells that express JIP-1 in vivo. A number of methods have been developed for delivering antisense DNA or RNA to cells. For example, antisense molecules can be injected directly into specific tissue sites. Modified antisense molecules, designed to target the desired cells (e.g., antisense linked to peptides or antibodies that specifically bind receptors or antigens expressed on the target cell surface) can be administered systemically.

One approach to achieving intracellular concentrations of the antisense molecule sufficient to suppress translation of endogenous mRNAs is to use a recombinant DNA construct in which the antisense oligonucleotide is placed under the control of a strong pol III or pol II promoter. The use of such a construct to transfect target cells in a patient will result in the transcription of sufficient amounts of single stranded RNAs that will form complementary base pairs with the endogenous JIP-1 transcripts, and thereby prevent translation of the JIP-1 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., *Nature*, 290:304 (1981)); the promoter contained in the 3' long terminal repeat of Rous sarcoma virus (Yamamoto et al., *Cell*, 22:787–797 (1988)); the herpes thymidine kinase promoter (Wagner et al., *Proc. Natl. Acad. Sci USA*, 78:1441, 1981); or the regulatory sequences of the metallothionein gene (Brinster et al., *Nature*, 296:39 (1988)).

Any type of plasmid, cosmid, YAC, or viral vector can be used to prepare the recominant DNA construct which can be introduced directly into specific tissue sites. Alternatively, viral vectors can be used that selectively infect the desired tissue (e.g., for brain, herpesvirus vectors may be used), in which case administration can be accomplished by another route (e.g., systemically).

Ribozymes

Ribozyme molecules designed to catalytically cleave JIP-1 mRNA transcripts also can be used to prevent translation of JIP-1 mRNA and expression of JIP-1 protein (see, e.g., PCT Publication WO 90/11364; Saraver et al., *Science*, 247:122 (1990)). While various ribozymes that cleave mRNA at site-specific recognition sequences can be used to destroy JIP-1 mRNAs, the use of hammerhead ribozymes is preferred. Hammerhead ribozymes cleave mRNAs at locations dictated by flanking regions that form complementary base pairs with the target mRNA. The sole requirement is that the target mRNA contain the following sequence of two bases: 5'-UG-3'. The construction and production of hammerhead ribozymes is well known in the art (Hasseloff et al., *Nature*, 334;585, 1988).

The ribozymes of the present invention also include RNA endoribonucleases (hereinafter "Cech-type ribozymes"), such as the one that occurs naturally in Tetrahymena Thermophila (known as the IVS or L-19 IVS RNA), which have been extensively characterized by Cech and his collaborators. See, e.g., Zaug et al., *Science*, 224:574 (1984); Zaug et al., *Science*, 231:470 (1986); Zaug et al., *Nature*, 324:429 (1986); PCT Application No. WO 88/04300; and Been et al., *Cell*, 47:207 (1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in JIP-1. In general, target sites for ribozymes are regions that are predicted to lack appreciable secondary structure. Target sites for ribozymes include:

5' GGUAUCGAUAAGCUUGAUAUCGCUGUC-CGGAGC 3' (SEQ ID NO:29) and

5' AGAGGCACUGUCCCAUCCUGGGCCUGU-UUCAUG 3' (SEQ ID NO:30).

As in the antisense approach, the ribozymes can be composed of modified oligonucleotides (e.g., for improved stability, targeting, etc.), and should be delivered to cells which express JIP-1 in vivo. A preferred method of delivery involves using a DNA construct "encoding" the ribozyme under the control of a strong constitutive pol III or pol II promoter, so that transfected cells will produce sufficient quantities of the ribozyme to destroy endogenous JIP-1 messages and inhibit translation. Because ribozymes, unlike antisense molecules, are catalytic, a lower intracellular concentration is required for efficiency. Destruction of JIP-1 mRNA would be advantageous in increasing apoptosis in tumors; in altering the cell damage occurring during ischemic reperfusion in cardiovascular disease, kidney disease, and stroke; and altering cell damage occurring in the liver in response to metabolic oxidative stress.

Other Methods for Reducing JIP-1 Expression

Endogenous JIP-1 gene expression can also be reduced by inactivating or "knocking out" the JIP-1 gene or its promoter using targeted homologous recomination (see, e.g., U.S. Pat. No. 5,464,764). For example, a mutant, non-functional JIP-1 (or a completely unrelated DNA sequence) flanked by DNA homologous to the endogenous JIP-1 gene (either the coding regions or regulatory regions of the JIP-1 gene) can be used, with or without a selectable marker and/or a negative selectable marker, to transfect cells that express JIP-1 in vivo. Insertion of the DNA construct, via targeted homologous recombination, results in inactivation of the JIP-1 gene. Such approaches are particularly suited for use in the agricultural field where modifications to ES (embryonic stem) cells can be used to generate animal offspring with an inactive JIP-1. However, this approach can be adapted for use in humans, provided the recombinant DNA constructs are directly administered or targeted to the required site in vivo using appropriate viral vectors, e.g., herpes virus vectors for delivery to brain tissue.

Alternatively, endogenous JIP-1 gene expression can be reduced by targeting deoxyribonucleotide sequences complementary to regulatory regions of the JIP-1 gene (e.g., a JIP-1 promoter and/or enhancer to form triple helical structures that prevent transcription of the JIP-1 gene in target cells in the body. See, e.g., Helene, *Anticancer Drug Des.* 6:569 (1981); Helene et al., *Ann N.Y. Acad. Sci.* 660:27 (1992); Maher, *Bioassays* 14:807 (1992).

Identification of Proteins that Interact with JIP-1

The invention also features polypeptides that interact with JIP-1. Any method suitable for detecting protein-protein interactions can be employed for identifying intracellular or extracellular proteins that interact with JIP-1. Among the traditional methods that can be employed are co-immunoprecipitation, crosslinking, and co-purification through gradients or chromatographic columns of cell lysates, or proteins obtained from cell lysates. Purified proteins are used to identify proteins in the lysate that interact with JIP-1. For these assays, the JIP-1 polypeptide can be full length JIP-1, a soluble domain of JIP-1, or some other suitable JIP-1 polypeptide.

To characterize JIP-1 interacting proteins, portions of their amino acid sequences can be ascertained using techniques well known to those of skill in the art, such as the Edman degradation technique. The amino acid sequences obtained can be used to design degenerate oligonucleotide probes that can be used to screen for gene sequences encoding the interacting protein. Screening may be accomplished, for example, by standard hybridization or PCR techniques. Techniques for the generation of degenerate oligonucleotide mixtures and screening are well-known. See Ausubel, supra; and Innis et al., eds., *PCR Protocols: A Guide to Methods and Applications,* Academic Press, Inc., New York (1990).

Additionally, methods can be used that result directly in the identification of genes that encode proteins that interact with JIP-1. These methods include, for example, screening expression libraries in a manner similar to the well known technique of antibody probing of λgt11 libraries using labeled JIP-1 polypeptides or a JIP-1 fusion protein, e.g., an JIP-1 polypeptide or domain fused to a marker such as an enzyme, a fluorescent dye, a luminescent protein, or to an IgFc domain.

Protein interactions can also be identified in vivo using the two-hybrid system. Chien et al., *Proc. Natl. Acad. Sci. USA,* 88:9578 (1991). A kit for practicing this method is available from Clontech (Palo Alto, Calif.). In this system, two plasmids, each encoding a hybrid protein, are constructed. One plasmid, the "bait" plasmid, includes a nucleotide sequence encoding the DNA-binding domain of a transcription activator protein fused to a nucleotide sequence encoding a protein of interest. The other plasmid includes a nucleotide sequence encoding the transcription activator protein's activation domain and an unknown protein, which may bind the protein of interest. The plasmids are transformed into a strain of *Saccharomyces cerevisiae* that contains a reporter gene (e.g., HIS or lacZ) whose regulatory region contains the transcription activator's binding site. Neither of the hybrid proteins can activate transcription of the reporter gene alone; the bait plasmid lacks an activation function, and the other plasmid cannot localize to the transcription activator's binding sites. If the protein of interest and the unknown protein form a protein-protein complex and reconstitute the proximity of the DNA binding domain and the activation domain, this complex can bind to the regulatory region of the reporter gene, and the reporter gene will be expressed.

The two-hybrid system or related methodology can be used to screen libraries for proteins that interact with the "bait" gene product. By way of example, JIP-1 can be used as the bait gene product. Total genomic or cDNA sequences are fused to the DNA encoding an activation domain of a transcriptional activator protein. This library and a plasmid encoding a hybrid of bait JIP-1 gene product fused to the DNA-binding domain are cotransformed into a yeast reporter strain, and the resulting transformants are screened for those that express the reporter gene. For example, a bait JIP-1 gene sequence, such as JIP-1 or a domain of JIP-1, can be cloned into a vector such that it is translationally fused to the DNA encoding the DNA-binding domain. of the GAL4 protein, to form a bait plasmid. Colonies are purified and the library plasmids responsible for reporter gene expression are isolated. The library plasmids are subjected to DNA sequencing to determine the sequences of the gene encoding the JIP-1 binding proteins.

As an example, a cDNA library can be made by methods that are routine in the art. This library can be inserted into vectors so that the sequences from the library are fused to nucleotide sequences encoding the transcriptional activation domain of the GAL4 protein. These vectors can then be co-transformed, along with a bait JIP-1 gene-GAL4 fusion plasmid, into a yeast strain which contains a lacZ gene driven by a promoter that contains the GAL4 activation sequence. If any of the library vectors encode hybrid proteins that bind the hybrid JIP-1 protein encoded by the bait plasmid, a functional GAL4 will be formed, and the HIS3 gene will be expressed. Colonies expressing HIS3 can then be purified, and used to produce and isolate the JIP-1 interacting protein using techniques routinely practiced in the art.

Therapeutic Compositions of JIP-1 Nucleic Acids, Peptides, and Polypeptides

Therapeutic compositions of the JNK inhibitor JIP-1 can be used to treat pathological conditions associated with apoptosis or transformation. These compositions can include JIP-1 polypeptides or peptides that specifically bind to and sequester JNK. Proteins can be purified by methods known to those skilled in the art. Ausubel, supra. Peptides can be synthesized by methods that are known to those skilled in the art. See, e.g., Merrifield, *J. Am. Chem. Soc.,* 85:2149–2154 (1963).

Peptide mimetics are also included in the therapeutic compositions of the invention. These compounds mimic the activity of the peptide or polypeptide, but are composed of molecules other than, or in addition to, amino acids. The design of such mimetics is described in, e.g., Hughes, *Philos. Trans. R. Soc. Lond.,* 290:387–394 (1980); Hodgson, *Biotechnol.,* 9:19–21 (1991); Suckling, *Sci. Prog.,* 75:323–359 (1991).

Therapeutic compositions of the invention also include nucleic acids encoding a JIP-1 polypeptide or peptide. These nucleic acids can be administered in a manner allowing their uptake and expression by cells in vivo. Compositions containing nucleic acids can be prepared for administration by methods that are routine in the art.

Therapeutic compositions of the invention can include one or more compounds, e.g., nucleic acids, peptides, polypeptides, or peptide mimetics and a pharmaceutically acceptable carrier. Pharmaceutically acceptable carriers are biologically compatible vehicles, e.g., physiological saline, which are suitable for administration to a patient.

Nucleic acids can be administered to the patient by standard vectors and/or gene delivery systems. Suitable gene delivery systems include liposomes, receptor-mediated delivery systems, naked DNA and viral vectors such as herpes viruses, retroviruses, adenoviruses and adeno-associated viruses.

Peptides can be coupled to membrane permeable peptides in order to facilitate their uptake by cells. This can be done by colinear synthesis of a membrane permeable peptide with a peptide sequence of interest. The two peptides could also be crosslinked together. Methods of coupling are described in, e.g., Lin et al., *J. Biol. Chem.,* 269:12320–12324 (1996); Rojas et al., *J. Biol. Chem.,* 271:27456–127461 (1997). Peptides can also be coupled to lipids to provide membrane permeability. See, e.g., Vijayaraghavan, *J. Biol. Chem.,* 272:4747–4752 (1997). As an example, a fatty acid can be coupled to the $\alpha$-$NH_2$ group of the peptide as an amide.

To enable the compositions to penetrate the blood-brain barrier, they can be delivered in encapsulated cell implants (e.g., those produced by CytoTherapeutics, Inc., Providence R.I.; see *Bioworld Today* 7:6 (Monday, Dec. 2, 1996)). Delivery of drugs to the brain can also be accomplished using RMP-7™ technology (Alkermes, Inc., Cambridge, Mass.; see Business Wire, "Third Major Agreement for Prolease Sustained Release Drug Delivery System," Dec. 2, 1996) or implantable wafers containing the drug (see PR Newswire, "Implantable Wafer is First Treatment to Deliver Chemotherapy Directly to Tumor Site," Sep. 24, 1996). The compositions can also be administered using an implantable pump for direct administration into intrathecal fluid (e.g., that made by Medtronic, Minneapolis, Minn.; see *Genetic Engineering News,* "Neurobiotechnology Companies Focus Programs on Pain and Neuroprotection," Nov. 1, 1996).

Administration of Therapeutic Compositions

Parenteral administration, such as intravenous, subcutaneous, intramuscular, or intraperitoneal delivery routes can be used to deliver the therapeutic compositions of the invention. Dosages for particular patients depend upon many factors, including the patient's size, body surface area, age, the particular substance to be administered, time and route of administration, general health and other drugs being administered concurrently. The amount of therapeutic composition to be administered to a patient can be in the range of 1 to 1000 $\mu$g/kg of body weights e.g., 10 to 500 $\mu$g/kg, or 20 to 200 $\mu$g/kg of body weight. A typical dose of peptide or nucleic acid to be administered to a patient is 100 $\mu$g per kilogram of body weight.

EXAMPLES

Example 1

Identification of JIP-1

The yeast two hybrid method was used to screen a mouse embryo cDNA library to identify proteins that interact with JNK. The method is described in detail in Fields et al., *Nature,* 340:245 (1989). The yeast strain used was L40 (MATa his$\Delta$200 trp1-901 leu2-3,112 ade2 LYS::(lexAop)$_4$-HIS URA3::(lexAop)$_8$-lacZ. Vojtek, et al., *Cell,* 74:205 (1993). Human JNK1 fused to the LexA DNA binding domain was used as the bait. The bait plasmid, pLexA-JNK1, was constructed by blunt-end ligation of a XbaI/HindIII fragment of pCMV-Flag-JNK1 (Derijard et al., *Cell,* 76:1025 (1994); Sluss et al., *Mol. Cell Biol.,* 14:8376 (1994); Gupta et al., *EMBO. J.,* 15:2760 (1996)) into the vector pBTM116 at the SmaI and SalI sites. Yeast transformants ($5.2\times10^6$) were examined for growth on media with 25 mM 3-aminotriazole in the absence of histidine. Positive clones were confirmed by measurement of lacZ expression.

The two-hybrid screen yielded a cDNA fragment encoding a portion of a JNK binding protein. A group of 7 independent clones, corresponding to overlapping fragments of this cDNA, was identified by sequencing. Full-length cDNA clones were obtained by screening a mouse brain λZAPII cDNA library (Stratagene Inc.) with a random-primed cDNA fragment corresponding to base pairs 560–1020 of the full length cDNA. Isolated cDNA clones were sequenced using an Applied Biosystems model 373A machine. The sequence of the 5' GC-rich non-coding region of the largest cDNA clone was confirmed using the Maxam-Gilbert method. Maxam et al., *Proc. Natl. Acad. Sci. USA*, 74:560–564 (1977). The amino acid sequence of the encoded protein was deduced from the cDNA sequence. Single letter abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

The largest cDNA clone isolated from the mouse brain library was 2790 base pairs in length, and contained a predicted coding region of 660 amino acids in the same reading frame as the partial clones obtained in the two-hybrid screen. The protein encoded by this cDNA, designated JNK interacting protein-1 (JIP-1), contains an amino terminal JNK binding domain (defined by the overlapping 2-hybrid clones) and a putative SH3 domain in the carboxy terminus. The structure and amino acid and nucleotide sequences of JIP-1 are shown in FIGS. 1A–1C. The JNK binding domain (JBD; residues 127–281, SEQ ID NO:4) and the putative SH3 domain (residues 491–540, SEQ ID NO:13) are indicated by boxes. The putative SH3 domain of JIP-1 is highly related to the SH3 domains located in the tyrosine kinase c-fyn and the p85 subunit of PI-3' kinase.

Human homologs of the murine JIP-1 gene can be isolated using the murine JIP-1 cDNA clones or fragments of those clones as probes, by methods that are routine in the art of molecular biology. For example, a library of human cDNA can be screened with a fragment of murine JIP-1 cDNA, and human cDNA hybridizing to the murine JIP-1 cDNA can be isolated, cloned, sequenced and analyzed for structural and functional similarity to murine JIP-1. For general methods, of isolating and characterizing homologous genes from libraries, see Sambrook et al., *Molecular Cloning, A Laboratory Manual*, Cold Spring Harbor Laboratory Press, Cold Spring Harbor, N.Y. (2d ed. 1989).

The tissue distribution of JIP-1 mRNA was examined by Northern blot analysis of poly (A)$^+$ RNA isolated from different murine tissues. Northern blots were performed using 2 μg of polyA$^+$ RNA isolated from various murine tissues (Clontech). The blots were hybridized to a probe that was prepared by labeling JIP-1 cDNA (base pairs 515–970) with [α-$^{32}$P]dCTP (Amersham International PLC) by the random priming method (Stratagene Inc.) according to the manufacturer's instructions. The integrity of the mRNA samples was confirmed by hybridization to an actin probe. The blots were washed three times with 1×SSC, 0.05% SDS, and 1 mM EDTA prior to autoradiography. The results indicate that JIP-1 is expressed in many different tissues, including brain, heart, spleen, lung, liver, muscle, kidney and testis. Highest amounts of JIP-1 mRNA were detected in brain, kidney, and testis.

Example 2
JIP-1 Specifically Binds JNK in vivo

To test whether JIP-1 and JNK interact in vivo, co-immunoprecipitation analysis was performed. COS-1 cells were mock-transfected or transfected with JIP-1 and JNK1 expression vectors. Constructs expressing epitope (HA) tagged JNK1 have been described previously. Dérijard et al., supra; Sluss et al., supra; Gupta et al., supra. Mammalian JIP-1 expression vectors were constructed by subcloning the JIP-1 cDNA into the XbaI and HindIII sites of pCMV5 and the HindIII and EcoRI sites of pcDNA3 (Invitrogen Inc.). DNA encoding the Flag epitope, -Asp-Tyr-Lys-Asp-Asp-Asp-Asp-Lys- (SEQ ID NO:14) (Immunex Corp.), was inserted into JIP-1 cDNA between the DNA encoding the first two codons of JIP-1 using insertional overlapping polymerase chain reaction (PCR). Ho et al., *Gene*, 77:51 (1989). Bacterial JIP-1 expression vectors were constructed by subcloning PCR fragments of the JIP-1 cDNA into the EcoRI and XbaI sites of pGEX-3X (Pharmacia LKB Biotechnology Inc.). GST fusion proteins were purified by affinity chromatography on GSH-agarose as described previously. Smith et al., *Gene*, 67:31 (1988). Sequences of the constructs were confirmed using an Applied Biosystems model 373A machine.

For the co-immunoprecipitation experiments, transfected or mock-transfected cells were irradiated with or without UV-C (40 J/m$^2$) and incubated for one hour. Lysates prepared from the cells were examined by protein immunoblot analysis using a mixture of antibodies specific for Flag and HA to detect Flag-JIP-1 and HA-JNK1, respectively. Cells were lysed in TLB (20 mM Tris (pH 7.5), 1% Triton X-100, 10% glycerol, 0.137 M NaCl, 25 mM sodium β-glycerophosphate, 1 mM sodium orthovanadate, 2 mM sodium pyrophosphate, 2 mM EDTA, 10 μg/ml leupeptin, 1 mM phenylmethylsulfonylfluoride). Soluble extracts were prepared by centrifugation at 100,000×g for 30 minutes at 4° C. The extracts were pre-cleared using protein G-Sepharose (Pharmacia-LKB Biotechnologies Inc.) and incubated for one hour with monoclonal antibody to the Flag epitope (M2; IBI-Kodak) or the HA epitope (12CA5; Boehringer-Mannheim) pre-bound to protein G-Sepharose. The immunoprecipitates were washed three times with TLB and once with 25 mM Hepes (pH 7.5), 0.2% (w/v) Triton X-100, 1 mM EDTA. Proteins were fractionated by SDS-PAGE and transferred electrophoretically to Immobilon-P membranes (Millipore). The membranes were blocked with 10% gamma globulin-free horse serum (Gibco-BRL) and probed with the M2 monoclonal antibody, to detect Flag-JIP-1, and either the 12CA5 monoclonal antibody or a sheep anti-JNK polyclonal antibody, to detect HA-JNK1. Immune complexes were detected with a second antibody coupled to horseradish peroxidase and enhanced chemiluminescence (Amersham International PLC).

JIP-1 was detected in JNK1 immunoprecipitates by protein immunoblot analysis, and JNK1 was detected in JIP-1 immunoprecipitates. Co-immunoprecipitation of JIP-1 with JNK2, was also observed. These data indicate that JIP-1 specifically binds JNK in vivo. Exposure to UW radiation caused no significant change in the amount of the JNK/JIP-1 complex detected by co-immunoprecipitation analysis. Control experiments performed to examine the specificity of the interaction of JIP-1 with JNK demonstrated that the related MAP kinases ERK2 and p38 did not co-immunoprecipitate with JIP-1. The absence of co-immunoprecipitation of JIP-1 with these MAP kinases demonstrates that JIP-1 forms a specific complex with JNK.

This same assay can be used to determine whether a specific polypeptide is a JIP-1 polypeptide.

Example 3
JIP-1 Interacts Directly with JNK

To test whether JIP-1 interacts directly with JNK, in vitro binding assays were performed. The putative JNK binding domain (JBD; amino acid-residues 127–281 of JIP-1), defined by the clones obtained in the two-hybrid screen, was expressed as a glutathione-S-transferase (GST) fusion protein. GST-fusion proteins were purified by affinity chromatography on GSH-agarose as described previously. Smith et al., Gene, 67:31 (1988). Recombinant JNK, prepared by in vitro translation in the presence of [$^{35}$S]methionine (Dérijard et al., supra; Sluss et al., supra; Gupta et al., supra), was incubated with GST-JIP-1 immobilized on GSH-agarose. Control experiments revealed no detectable binding of JNK isoforms to GST alone. In contrast, in assays using GST-JNK fusion proteins representing ten different human JNK isoforms, each of these proteins exhibited similar amounts of binding to JIP-1. JIP-1 therefore interacts with multiple JNK isoforms.

Previous studies have demonstrated that JNK binds to the transcription factors c-Jun and ATF2, and that the binding of JNK to these transcription factors is isoform-dependent. To test whether JIP-1 binding to JNK is also isoform-dependent, a binding assay was utilized. Cell lysates (1 ml in TLB) containing JNK1, JNK2, or p38 MAP kinase, each tagged with the Flag epitope, were incubated with 5 $\mu$g GST-fusion proteins pre-bound to 10 $\mu$l glutathione-Sepharose. The GST fusion proteins used contain residues 127–202 (SEQ ID NO:15), 203–281 (SEQ ID NO:16), 164–240 (SEQ ID NO:17), or 127–281 (SEQ ID NO:4) of JIP-1. The GST-ATF2 fusion protein contains residues 1–109 of ATF2, and the GST-Jun fusion protein contains residues 1–79 of c-Jun. After incubation for one hour at 4° C. and three washes with TLB, bound proteins were detected by protein immunoblot analysis with the M2 monoclonal antibody, which is specific for the Flag epitope. Dérijard, et al., supra; Sluss et al., supra; Gupta et al., supra. When ATF2 or c-jun GST fusion proteins were used in this assay, binding to JNK1 was greater than binding to JNK2. This finding is consistent with the results of previous studies. In contrast, when GST-JIP-1 fusion proteins containing residues 127–202 or 127–281 of JIP-1 were tested in the assay, these proteins bound both JNK1 and JNK2. The level of binding of these fusion proteins to JNK1 was similar to the level of binding to JNK2. The binding of JNK to JIP-1 was significantly greater than the binding of JNK to ATF2 or c-Jun. Control experiments demonstrated that JIP-1 did not bind to p38 MAP kinase. These data establish that JIP-1 binding to JNK1 is quantitatively similar to JIP-1 binding to JNK2, and that JNK binding to JIP-1 is significantly greater than JNK binding to the transcription factors ATF2 and c-Jun.

The GST-JIP-1 fusion proteins containing various portions of the JIP-1 gene were used to define regions of JIP-1 that are required for JNK interaction. A GST-JIP-1 fusion protein containing residues 127–281 of JIP-1 bound both JNK1 and JNK2. No JNK binding was detected in experiments using the central region (residues 164–240) or the carboxy terminal region (residues 203–281) of JIP-1. However, JNK binding activity was observed in experiments using the amino terminal region (residues 127–202 of JIP-1). These data indicate that residues 127–164 of JIP-1 are required for JNK binding activity.

To more precisely define the JIP-1 sequence required for JNK binding activity, additional GST-JNK fusion proteins were constructed. These fusion proteins contained residues 135–202 (SEQ ID NO:18), 144–202 (SEQ ID NO:19), 154–202 (SEQ ID NO:20), 164–202 (SEQ ID NO:21), 127–143 (SEQ ID NO:22), 127–153 (SEQ ID NO:23), or 127–163 (SEQ ID NO:24) of JIP-1. Proteins containing residues 127–202, 135–202, 144–202, 154–202, and 127–163 all bound both JNK1 and JNK2. Thus, JIP-1 residues 144–163 are important for the interaction of JIP-1 with JNK. As shown in FIG. 2, this region of JIP-1 shares sequence similarity with the JNK binding domains of ATF2 and c-Jun.

This assay can also be used to analyze a given polypeptide to determine whether it is, or is not, a JIP-1 polypeptide.

Example 4
A Small NH$_2$-terminal Region of JIP-1 is Sufficient for Interaction with JNK The effect of increasing concentrations (0, 4, 8, 16, 32, and 64 $\mu$g/ml) of a synthetic peptide corresponding to JIP-1 residues 148–174 (SEQ ID NO:3) or a control peptide having a scrambled sequence (SEQ ID NO:12) on JIP-1-JNK interaction was examined. Peptides were synthesized using an Applied Biosystems machine. Cell lysates containing Flag epitope-tagged JNK were incubated with GST-JIP-1 (residues 127–281) prebound to glutathione-Sepharose. The beads were washed, and bound proteins were detected by protein immunoblot analysis with a Flag-specific antibody. While the control peptide had no effect, incubation with the synthetic peptide corresponding to residues 148–174 of JIP-1 resulted in a dose-dependent decrease in JIP-1 binding to JNK1, indicating that this peptide competes with JIP-1 for binding to JNK.

The JNK binding domain of JIP-1 contains three amino acids, Lys-155, Thr-159, and Leu-160, that are conserved in the JNK binding domains of ATF2 and c-Jun (FIG. 2). A hydrophobic amino acid, Leu, is found at residue 162 of JIP-1. ATF2 and c-Jun also contain hydrophobic amino acids (ATF2, Phe; c-Jun, Leu) in the position corresponding to residue 162 of JIP-1. To test if these conserved residues are involved in JNK binding, the wild type JIP-1 JBD (residues 148–174) was substituted with glycines in these positions to produce the peptides shown in FIG. 3 (SEQ ID NOs:7–11). The mutant peptides are identical to the wild type peptide except for the indicated glycine substitutions. The binding of JNK1 to GST, as well as a GST fusion protein containing JIP-1 residues 127–281, was examined in the absence and presence of the synthetic peptides (64 $\mu$g/ml). A peptide with a scrambled sequence (SEQ ID NO:12) was used as a control. The peptide representing the wild-type JIP-1 sequence caused a dose-dependent inhibition of JIP-1 binding to JNK. In contrast, the control peptide caused no change in JNK binding. When any of the glycine-substituted peptides was used in the assay, the inhibition of JNK binding was greatly reduced compared to that observed with the wild type peptide. These data indicate that Lys-155, Thr-159, Leu-160, and Leu-162 are involved in JIP-1 binding to JNK.

Example 5
JIP-1 is a Selective Inhibitor of JNK Activity

To test whether JIP-1 competes with Jun and ATF2 for interaction with JNK, the effect of JIP-1 on transcription factor-mediated phosphorylation of exogenous substrates was analyzed using an in vitro protein kinase assay. In these experiments, Chinese hamster ovary (CHO) cells were serum-starved for one hour. In some experiments, the cells were treated with 10 ng/ml mouse interleukin 1 or 100 nM phorbol myristic acetate. JNK, p38, and ERK protein kinase activity was measured in an immune complex kinase assay using 3 $\mu$g of the substrates GST-Jun, GST-ATF2, and myelin basic protein (MBP), respectively. Protein kinase assays were performed using 40 $\mu$l 20 mM Hepes (pH 7.4), 20 mM MgCl$_2$, 20 mM $\beta$-glycerophosphate, 2 mM dithiothreitol, 0.1 mM sodium orthovanadate, 50 $\mu$M [$\gamma$-$^{32}$P] ATP (10 Ci/mmol). After incubation for 30 minutes at 30° C., phosphorylation of substrates was analyzed by polyacrylamide gel electrophoresis and autoradiography.

The results show that JIP-1 markedly inhibited the phosphorylation of c-Jun by JNK. However, JIP-1 caused no significant change in the phosphorylation of substrates by the related MAP kinases p38 and ERK2. JIP-1 is thus a selective inhibitor of JNK.

This same assay can be used to determine whether a specific polypeptide has the same phosphorylation function of wildtype JIP-1.

Example 6
Expression of JIP-1 Inhibits Targets of the JNK-regulated Signal Transduction Pathway The effect of JIP-1 on targets of the JNK signal transduction pathway, including the transcription factors c-Jun, ATF2 and Elk-1, was examined to determine whether JIP-1 inhibits signal transduction by JNK.

In these experiments, CHO cells were cotransfected with constructs encoding the transcription factors and JIP-1 using previously described methods. Dérijard et al., supra; Sluss et al., supra; Gupta et al., supra. A luciferase reporter plasmid was used to monitor the expression of the transcription factors. Transfection efficiency was determined using a β-galactosidase expression vector. Constructs used in these experiments included GAL4 fusions with the c-myc, Sp1 and VP16 activation domains (described in Whitmarsh et al., Science, 269:403 (1995); Davis, Science, 269:403 (1995); Gille et al., Curr. Biol., 5:1191 (1995)). Other constructs used were GAL4-c-Jun, in which GAL4 is fused to c-Jun; GAL4-c-Jun (S63A/S73A), in which GAL4 is fused to a mutant c-Jun in which the serines at positions 63 and 73 have been changed to alanines; GAL4-ATF2, in which GAL4 is fused to wild type ATF2 (ATF2(Thr-69,71)); GAL4-ATF2 (T69A/T71A) (ATF2(Ala-69/71)), in which GAL4 has been fused to a mutant ATF2 in which the tyrosines at positions 69 and 71 have been changed to alanines; GAL4-Elk-1, in which GAL4 has been fused to Elk-1; and GAL4-Elk-1 (S383A), in which GAL4 has been fused to a mutant Elk-1 in which the serine at position 383 has been changed to an alanine. Gupta et al., EMBO J, 15:2760–2770 (1996); Raingeaud et al., Mol. Cell. Biol., 16:1247–1255 (1996); Whitmarsh et al., Science, 269:403–407 (1995).

Insertional overlapping PCR, described in detail in Ho, supra, was used to construct expression vectors for the JNK binding domain (JBD; amino acid residues 127–281) of JIP-1 and for a mutant JIP-1 lacking the SH3 (amino acid residues 491–540) domain.

Figure 4B:
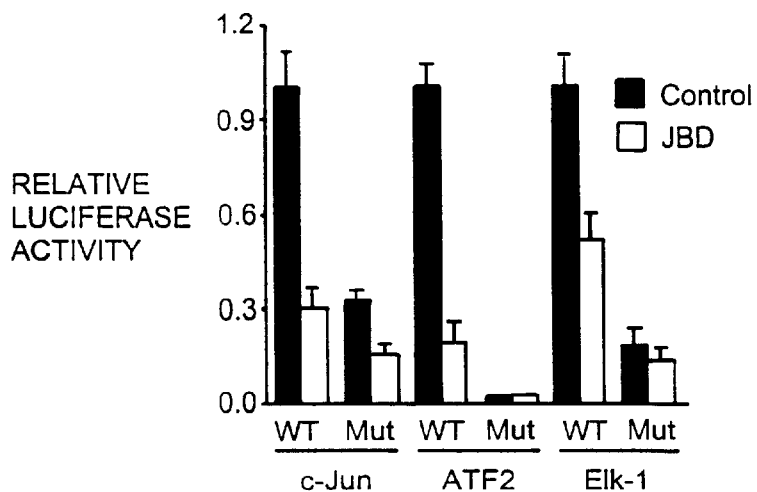
FIG. 4B is a bar graph showing the effect of recombinant JBD (JIP-1 residues 127–281) on reporter gene expression mediated by wild type and mutant forms of GAL4-c-Jun, GAL4-ATF2, and GAL4-Elk-1.
Figure 4C:
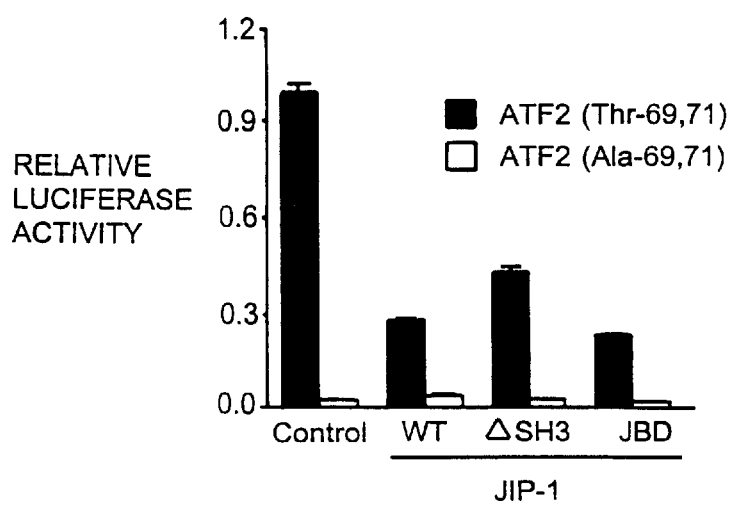
FIG. 4C is a bar graph showing the effect of wild type and mutant JIP-1 and JBD on reporter gene expression mediated by wild type and mutant GAL4-ATF2.

Transfected cells were activated by treatment with 10% (v/v) fetal calf serum, and luciferase and β-galactosidase activities were measured in cell lysates at 48 hours post-transfection. The results are shown in FIGS. 4A–4C. The data are presented as the ratio of luciferase activity (light units) to β-galactosidase activity (OD units) measured in the cell extracts (mean±SEM (n=3)), and are normalized to the luciferase activity detected in the absence of JBD (FIGS. 4A and 4B) or ATF2 (FIG. 4C).

Control experiments demonstrated that the JNK binding domain (JBD; residues 127–281 of JIP-1) did not inhibit reporter gene expression mediated by the activation domains of c-Myc, E1a, Sp1, and VP16 (FIG. 4A). Significant inhibition of c-Jun and ATF2 transcriptional activity by JIP-1 was observed, however (FIG. 4B). The partial inhibition of Elk-1 transcriptional activity shown in FIG. 4B may reflect an association of both ERK and JNK MAP kinases with Elk-1 regulation. Mutation of the JNK phosphorylation sites in ATF2, c-Jun, and Elk-1 caused lower basal transcriptional activity that was not markedly inhibited by JIP-1.

As shown in FIG. 4C, inhibition of JNK-regulated gene expression was observed in experiments using wild-type JIP-1, the JNK binding domain (JBP), and ASH3, a JIP-1 deletion mutant lacking the SH3 domain. Together, these data indicate that JIP-1 suppresses JNK-regulated gene expression, and that the JNK binding domain is sufficient for this activity.

This assay can be used to determine whether specific polypeptides have the same effect on signal transduction as full length, wildtype JIP-1.

Example 7
Subcellular Distribution of JIP-1

The subcellular distribution of JIP-1 was analyzed by performing indirect immunofluorescence on JIP-1-expressing cells. In these experiments, the cells were grown on coverslips, fixed with 4% paraformaldehyde, permeabilized with 0.25% Triton X-100, and processed for immunofluorescence microscopy. JIP-1 was detected in the cytoplasm, but not the nucleus, of control and UV-irradiated cells. In contrast, JNK is detected in both the cytoplasmic and nuclear compartments.

It is likely that it is JNK in the nucleus which is involved in the regulation of gene expression. Since JIP-1 is cytoplasmic, it was unclear how it could inhibit the nuclear function of JNK. To investigate the mechanism of JIP-1 action, the distribution of JNK was examined in cells that had been transfected with either hemagglutinin (HA)-tagged JNK1 (HA-JNK1) alone, or HA-JNK1 and Flag-tagged JIP-1 (Flag-JIP-1). In these experiments, the cells were exposed to a potent JNK activator (40 J/$^2$ UV-C) for one hour prior to processing for immunofluorescence. The primary antibodies used were rabbit anti-HA (12CA5; Boehringer Mannheim), which recognizes HA-tagged JNK1; and mouse monoclonal anti-Flag (M2; IBI-Kodak), which recognizes Flag-tagged JIP-1. The secondary antibodies were Texas Red-goat anti-mouse Ig and fluoroscein isothiocyanate-conjugated donkey anti-rabbit Ig (Jackson Immunoresearch). Procedures for digital imaging microscopy and image restoration using the exhaustive photon reassignment algorithm are described in Carrington et al., Science, 268:1483 (1995). Individual optical sections were inspected using computer graphics software on a Silicon Graphics workstation.

The results demonstrate that expression of JIP-1 reduces the amount of nuclear JNK detected in control and UV-irradiated cells. In contrast, JIP-1 expression has no significant effect on the subcellular distribution of p38 MAP kinase, which is also located in both nuclear and cytoplasmic compartments of cultured cells. These data indicate that JIP-1 expression results in selective cytoplasmic retention of JNK. It is likely that this cytoplasmic retention contributes to the ability of JIP-1 to inhibit JNK-mediated signal transduction.

Example 8
JIP-1 Inhibits Nerve Growth Factor Withdrawal-Induced Apoptosis

The effect of JIP-1 on this biological response was investigated to determine whether JIP-1 inhibits the biological effects of the JNK signaling pathway. NGF withdrawal-induced apoptosis of differentiated PC12 cells was examined following transfection with the expression vectors pCDNA3 (control) and pCDNA3-Flag-JIP-1 (containing residues 127–281 of JIP-1) using methods described previously. Xia et al., Science, 270:1326 (1995). The percentage of apoptotic cells in the total transfected cell population was blind-scored and quantitated. This assay scores adherent cells with an apoptotic morphology at 17 hours following NGF withdrawal. Cells that have completed apoptosis are nonadherent and are not scored. Thus, while the cumulative extent of apoptosis is large (100%), lower numbers of apoptotic cells are detected at a single time point.

Figure 5:
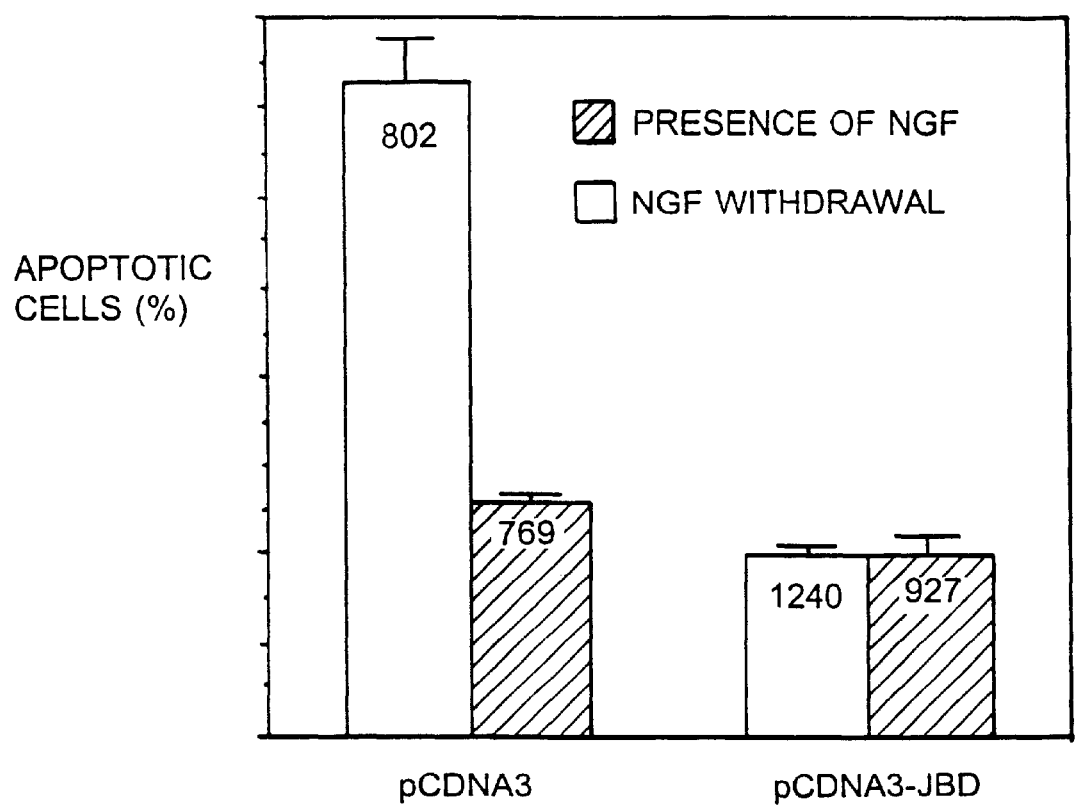
FIG. 5 is a bar graph showing the effect of the JBD of JIP-1 on Nerve Growth Factor (NGF) withdrawal-induced apoptosis.

The results are shown in FIG. 5. The data shown are representative of three independent experiments. The error bars in the graph indicate the SEM and the numbers within each bar are the total number of transfected cells counted. Expression of the JNK binding domain of JIP-1 (JBD; residues 127–281) in differentiated PC12 cells markedly reduced apoptosis following NGF-withdrawal. These data demonstrate that JIP-1 suppresses JNK-mediated signal transduction. This assay can be used to test new JIP-1 polypeptides.

Example 9
JIP-1 Inhibits Pre-B Cell Transformation by BCR-ABL

The BCR-ABL oncogene, which is associated with chronic myelogenous leukemia (CML), causes JNK activation in the absence of increased ERK activity. Raitano et al., *Proc. Natl. Acad. Sci. USA*, 92:11746 (1995). Oncogenic transformation by BCR-ABL may be mediated in part by the JNK signaling pathway. Since JIP-1 can inhibit JNK activity, the effect of JIP-1 expression on oncogenic transformation was examined. Plasmid vectors expressing v-ABL or BCR-ABL and Flag-tagged JBD (residues 127–281) of JIP-1 were used to transfect 293 cells. JNK activity was then measured in an immune complex kinase assay of lysates of the transfected 293 cells, using a polyclonal JNK antibody and GST-Jun as the substrate. Control experiments demonstrated that v-ABL and BCR-ABL caused constitutive JNK activation (approximately 5-fold), which was blocked by co-expression of the JBD of JIP-1. JIP-1 can therefore inhibit BCR-ABL-mediated activation of JNK.

Figure 6:
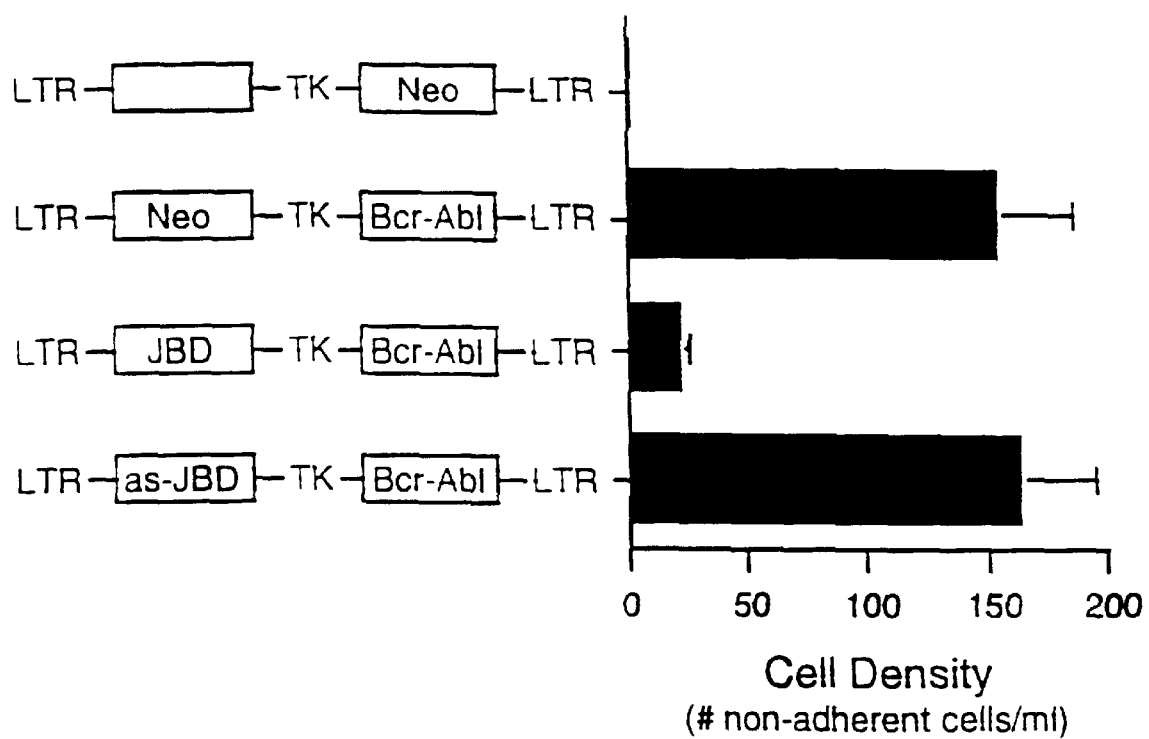
FIG. 6 is a bar graph showing the effect of bicistronic retroviruses on primary mouse bone marrow cells.

To examine the effect of JIP-1 on BCR-ABL-mediated cellular transformation, bone marrow transformation assays were performed using recombinant retroviruses packaged with 293T cells as described in Sawyers et al., *J. Exp. Med.*, 181:307 (1995). Bicistronic retroviruses expressing BCR-ABL, alone, or in combination with the Flag-tagged JBD (residues 127–281) of JIP-1, were prepared by subcloning p185BCR-ABL into the ClaI site of pSRαTK, downstream of the internal TK promoter, to create pSRαMSVTKp185. The JBD was subcloned into the upstream EcoRI site in the sense and antisense orientations. The structures of the retroviral constructs are shown in FIG. 6.

Transfection of 293 cells with these retroviral constructs resulted in expression of the appropriate proteins, as demonstrated by immunoblot analysis of whole cell lysates using antibodies specific for ABL to detect BCR-ABL, and antibodies to Flag to detect the JBD of JIP-1. The recombinant retroviruses were then used to infect primary mouse marrow cells, and the transformation of pre-B cells was monitored in culture. FIG. 6 shows the mean density (±SE) of non-adherent pre-B cells on day 10 post infection. The data shown are derived from three independent experiments plated in triplicate. As expected, BCR-ABL caused pre-B cell transformation. The JBD of JIP-1 caused marked inhibition of transformation when present in the sense, but not the anti-sense, orientation. In some cultures infected with BCR-ABL and JBD, pre-B cell outgrowths were detected after 3–4 weeks, but these clones demonstrated no expression of JBD by protein immunoblot analysis. Since JIP-1 inhibits JNK signaling, these results indicate that the JNK pathway is required for pre-B cell transformation by BCR-ABL.

The demonstration that JNK is involved in both apoptosis and oncogenic transformation indicates that the biological actions of the JNK signal transduction pathway depend on the specific cellular context. The integration of JNK with other signal transduction pathways may be an important determinant of the functional consequences of JNK activation. The ability of JIP-1, an inhibitor of the JNK signal transduction pathway, to block both transformation and apoptosis is consistent with this hypothesis.

The physiological function of JIP-1 may be to suppress signal transduction by the JNK pathway. For example, JIP-1 may compete with substrates that bind JNK. Alternatively, JIP-1 may have a more direct role in targeting JNK to specific regions of the cell or to specific substrates. Since JIP-1 causes redistribution of JNK within the cell, JIP-1 may function as a cytoplasmic anchor for JNK. The tethering of JNK in the cytoplasm by interactions with JIP-1 provides a mechanism for controlling signal transduction by the JNK pathway, and the related phenomena of apoptosis and transformation.

This assay can be used to determine if specific polypeptides have the same effect on cellular transformation as full length, wildtype JIP-1.

Example 10
Screening for Peptides with JIP-1 Activity

Peptides suspected of having JIP-1 activity can be tested in the JNK binding assay described supra. Peptides are synthesized by methods that are well known to those skilled in the art; for example, using an Applied Biosystems synthesizer. Cell lysates containing Flag epitope-tagged JNK are incubated with GST-JIP-1 (residues 127–281) bound to glutathione-Sepharose, either with or without synthetic peptides (0, 4, 8, 16, 32 or 64 μg/ml), for one hour at 4° C. The beads are washed in TLB, and the bound proteins are detected by protein immunoblot analysis with a Flag-specific antibody, e.g., M2. Synthetic peptides with JIP-1 activity are those which inhibit the interaction of JIP-1 with JNK, as detected in this assay. These synthetic peptides should possess at least 60% of the binding activity of JIP-1.

Example 11
Therapeutic Applications

JIP-1 is shown herein to be capable of inhibiting apoptosis and transformation. Compositions containing JIP-1 polypeptides or nucleic acids can be administered to treat conditions characterized by these phenomena. Nucleic acids can be administered by, methods described in, e.g., Ausubel, et al., supra. A standard dosage would be from 1 to 1000 μg/kg of body weight. Polypeptides, peptides and peptide mimetics of the invention can be formulated according to procedures which are well known to those skilled in the art. A standard dosage of polypeptide also would be from 1 to 1000, e.g., 10 to 500, or 20 to 200 μg/kg of body weight.

Animal models for testing the effect of JIP-1 therapeutic compositions include the bcr-abl leukemia model. Daley et al., *Science*, 247:824–830 (1990). Other animal models that can be used include the myc/ras transformation model. Sinn et al., *Cell*, 49:465–475 (1987). Animal models for testing the effect of JIP-1 therapeutic compositions on conditions associated with apoptosis include a model of excitotoxic stress in the hippocampus, and a model of E2F-1 induced apoptosis. Ben-Ari et al., *Neuroscience*, 14:375–403 (1985); Field et al., *Cell*, 85:549–561 (1996). Other conditions that can be treated with JIP-1 compositions include liver damage (Mendelson et al., *Proc. Natl. Acad. Sci. USA*, 93:12908–12913 (1996)); kidney disease and organ transplantation (DeMari et al., *Am. J. Physiol.*, 272:F292–F298 (1997)); and heart disease (Pombo et al., *J. Biol. Chem.*, 269:26546–26551 (1994); Force et al., *Circ. Res.*, 78:947–953 (1996).

Example 12

Diagnostic Applications

The polypeptides and antibodies of the invention can be used to detect or monitor JIP-1 expression. Levels of JIP-1 protein in a sample can be assayed by any standard technique. For example, JIP-1 protein expression can be monitored by standard immunological or immunohistochemical procedures using the antibodies described herein. See, e.g., Ausubel et al., supra; Bancroft et al., *Theory and Practice of Histological Techniques*, Churchill Livingstone (1982). Alternatively, JIP-1 expression can be assayed by standard Northern blot analysis, or can be aided by PCR. See Ausubel, supra; Ehrlich, ed., *PCR Technology: Principles and Applications for DNA Amplification*, Stockton Press, New York. Point mutations in the JIP-1 sequence can be detected using well known nucleic acid mismatch detection techniques. Lower than normal levels of JIP-1 would have the effect of altering apoptosis, while higher than normal levels would cause immune suppression, altered inflammatory responses, and alterations in tumor growth.

Other Embodiments

The invention also includes naturally occurring and non-naturally-occurring allelic variants of JIP-1. Compared to the most common naturally occurring nucleotide sequence encoding JIP-1, the nucleic acid sequence encoding allelic variants may have a substitution, deletion, or addition of one or more nucleotides. The preferred allelic variants are functionally equivalent to naturally occurring JIP-1.

It is to be understood that while the invention has been described in conjunction with the detailed description thereof, that the foregoing description is intended to illustrate and not limit the scope of the invention, which is defined by the scope of the appended claims. Other aspects, advantages and modifications are within the scope of the following claims.

---

What is claimed is:

1. A substantially pure JNK-interacting protein 1 (JIP-1) polypeptide, the amino acid sequence of which comprises SEQ ID NO:1, or SEQ ID NO:1 with at least one conservative amino acid substitution, wherein the polypeptide specifically inhibits the activity of c-Jun NH$_2$ terminal kinase (JNK).

2. A substantially pure polypeptide, the amino acid sequence of which comprises SEQ ID NO:4, or SEQ ID NO:4 with at least one conservative amino acid substitution, wherein the polypeptide specifically inhibits the activity of c-Jun NH$_2$ terminal kinase (JNK).

3. The polypeptide of claim 2, wherein the polypeptide is modified by attachment of a hydrophobic moiety.

4. The polypeptide of claim 2, wherein the polypeptide is modified by attachment of a peptide that facilitates uptake of the polypeptide by a cell.

5. The polypeptide of claim 1, wherein the polypeptide is modified by attachment of a hydrophobic moiety.

6. The polypeptide of claim 1, wherein the polypeptide is modified by attachment of a peptide that facilitates uptake of the polypeptide by a cell.

7. A substantially pure polypeptide, the amino acid sequence of which comprises SEQ ID NO:3, or SEQ ID NO:3 with at least one conservative amino acid substitution, wherein the polypeptide specifically inhibits the activity of c-Jun NH$_2$ terminal kinase (JNK).

8. The polypeptide of claim 7, wherein the polypeptide is modified by attachment of a hydrophobic moiety.

9. The polypeptide of claim 7, wherein the polypeptide is modified by attachment of a peptide that facilitates uptake of the polypeptide by a cell.

10. A substantially pure polypeptide, the amino acid sequence of which comprises any one of SEQ ID NO:15, SEQ ID NO:18, SEQ ID NO:19, SEQ ID NO:20, or SEQ ID NO:24; or SEQ ID NO:15, SEQ ID NO:18, SEQ ID NO:19, SEQ ID NO:20, or SEQ ID NO:24 with at least one conservative amino acid substitution, wherein the polypeptide specifically inhibits the activity of c-Jun NH$_2$ terminal kinase (JNK).

11. The polypeptide of claim 10, wherein the polypeptide is modified by attachment of a hydrophobic moiety.

12. The polypeptide of claim 10, wherein the polypeptide is modified by attachment of a peptide that facilitates uptake of the polypeptide by a cell.

13. A substantially pure polypeptide, the amino acid sequence of which comprises any one of SEQ ID NO:13, SEQ ID NO:16, SEQ ID NO:17, SEQ ID NO:21, or SEQ ID NO:22; or SEQ ID NO:13, SEQ ID NO:16, SEQ ID NO:17, SEQ ID NO:21, or SEQ ID NO:22 with at least one conservative amino acid substitution.

14. The polypeptide of claim 13, wherein the polypeptide is modified by attachment of a hydrophobic moiety.

15. The polypeptide of claim 13, wherein the polypeptide is modified by attachment of a peptide that facilitates uptake of the polypeptide by a cell.

* * * * *